US011236072B2

(12) United States Patent
Riether et al.

(10) Patent No.: US 11,236,072 B2
(45) Date of Patent: *Feb. 1, 2022

(54) N-[(PYRIMIDINYLAMINO)PROPANYL]-,N-[PYRIDYLAMINO)PROPANYL]- AND N-[(PYRAZINYLAMINOL)PROPANYL] ARYLCARBOXAMIDES

(71) Applicant: Boehringer Ingelheim International GmbH, Ingelheim am Rhein (DE)

(72) Inventors: Doris Riether, Biberach an der Riss (DE); Marco Ferrara, San Donato Milanese (IT); Niklas Heine, Biberach an der Riss (DE); Uta Friederike Lessel, Maselheim (DE); Radoslaw Lipinski, Biberach an der Riss (DE); Stefan Scheuerer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 89 days.

This patent is subject to a terminal disclaimer.

(21) Appl. No.: 16/634,890

(22) PCT Filed: Jul. 26, 2018

(86) PCT No.: PCT/EP2018/070267
§ 371 (c)(1),
(2) Date: Jan. 29, 2020

(87) PCT Pub. No.: WO2019/025275
PCT Pub. Date: Feb. 7, 2019

(65) Prior Publication Data
US 2020/0231575 A1    Jul. 23, 2020

(30) Foreign Application Priority Data

Jul. 31, 2017   (EP) ..................... 17183978

(51) Int. Cl.
*C07D 401/12* (2006.01)
*C07D 401/14* (2006.01)
*C07D 403/12* (2006.01)

(52) U.S. Cl.
CPC ......... *C07D 403/12* (2013.01); *C07D 401/12* (2013.01); *C07D 401/14* (2013.01)

(58) Field of Classification Search
CPC ... C07D 401/12; C07D 401/14; C07D 403/12
See application file for complete search history.

(56) References Cited

U.S. PATENT DOCUMENTS 9,884,854 B2 * 2/2018 Riether ............... C07D 403/04

FOREIGN PATENT DOCUMENTS

| WO | 2003051872 A1 | 6/2003 |
| WO | 20160344882 | 3/2006 |
| WO | 2019025275 A1 | 2/2019 |

OTHER PUBLICATIONS

Sakurai, Howard Hughes Medical Institute, Orec=xins and Orexin Receptors: A family of Hypothalmix Neuropeptides and G protein Coupled Receptors, vol. 92, 1998.
DeGorce, CisbioBioassays, HTRF: A technology Tailored for Drug Discovery, vol. 3, 2009.
Trinquet, Analytical Biochem, D-myo-Inositol 1-phosphate as a surrogate of D-myo-inositol 1,4,5-tris phophate to monitor G protein-coupled receptor activation, vol. 358, 2006.
Sakurai, Department of Molecular Bioscience, The role of orexin in motivated behaviours, 2014.
Kishi, Suvorexant for Primary Insomnia, Dept. of Psychiatry, 2015.
Gotter, Pharmacological Review, International Union of Basic and Clinical Pharmacology, vol. 64, No. 3, 2012.
Bonaventure, Journal of Pharmacology, A selective Orexin-1 freceptor Antagonist attenuates stress-induced hyperarousal without hypnotic effects, 2015.
Roecker, Journal of Medicinal Chem, Orexin receptor Atagonists, 2019.
Chen, Dept. of Psyiology, Military Medical Univ., The hypocretin Orexin system, 2014.
Muschamp, karolinska Institutet, Orexin facilitates regard by attenuating the antireward effects of its cotransmitter dynorphin in ventral tegmental area, 2013.
Deleacea, Proc. nat. acad. Science, The hypocretins: hypothalamus-sepcific peptides with neuroexcitatory activity, vol. 95, 1998.
International Search Reprt for PCT/EP2018/070267 dated Oct. 5, 2018.

* cited by examiner

*Primary Examiner* — Brian E McDowell
(74) *Attorney, Agent, or Firm* — David L. Kershner

(57) ABSTRACT

The present invention relates to novel N-[(Pyrimidinylamino)propanyl]-, N-[(Pyridylamino)-propanyl]- and N-[(Pyrazinylamino)¬propanyl]arylcarboxamide such as compound

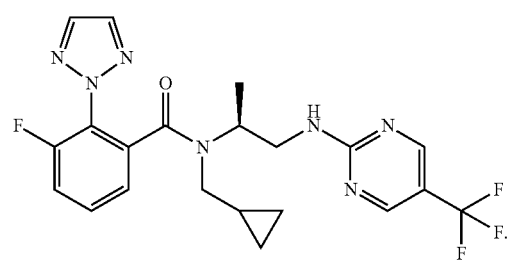

The present invention also relates to derivatives of such compounds, processes for their preparation, pharmaceutical compositions containing them and their use in therapy, particularly in the treatment or prevention of conditions having an association with the orexin sub-type 1 receptor.

5 Claims, No Drawings

N-[(PYRIMIDINYLAMINO)PROPANYL]-,N-[PYRIDYLAMINO)PROPANYL]- AND N-[(PYRAZINYLAMINOL)PROPANYL] ARYLCARBOXAMIDES

FIELD OF THE INVENTION

The present invention relates to novel N-[(Pyrimidinylamino)propanyl]-, N-[(Pyridylamino)-propanyl]- and N-[(Pyrazinylamino)propanyl]arylcarboxamide derivatives, processes for their preparation, pharmaceutical compositions containing them and their use in therapy, particularly in the treatment or prevention of conditions having an association with the orexin sub-type 1 receptor.

BACKGROUND OF THE INVENTION

Orexins are hypothalamic neuropeptides that play an important role in the regulation of many physiological behaviours such as arousal, wakefulness, appetite, food intake, cognition, motivated behaviours, reward, mood and stress. Orexin A, also referred to as hypocretin 1, is a peptide composed of 33 amino acids and orexin B, also referred to as hypocretin 2, is a peptide composed of 28 amino acids. Both are derived from a common precursor peptide referred to as pre-pro-orexin [Sakurai et al., Cell, 1998 Feb. 20; 92(4):573-85, and De Lecea et al., Proc. Nat. Acad. Sci., 1998 Jan. 6; 95(1):322-7). Orexins bind to two orphan G-protein-coupled receptors, the orexin receptor type 1 (OX1R) and orexin receptor type 2 (OX2R), which are widely distributed in the central nervous system and peripheral organs such as adrenal glands, gonads, and gut. Whereas orexin A binds predominantly to OX1R, orexin B is able to bind to both OX1R and OX2R.

Orexins are involved in the regulation of a wide range of behaviours including for example the regulation of emotion and reward, cognition, impulse control, regulation of autonomic and neuroendocrine functions, arousal, vigilance and sleep-wakefulness states (Muschamp et al., Proc. Natl. Acad. Sci. USA 2014 Apr. 22; 111(16):E1648-55; for a recent review see Sakurai, Nat. Rev. Neurosci., 2014; November; 15(11):719-31; Chen et al., Med. Res. Rev., 2015; January; 35(1):152-97; Gotter et al., Pharmacol. Rev., 2012, 64:389-420 and many more). Dual antagonism of OX1R and OX2R by small molecules is clinically efficacious in the treatment of insomnia, for which the drug suvorexant, [[(7R)-4-(5-chloro-1,3-benzoxazol-2-yl)-7-methyl-1,4-diazepan-1-yl][5-methyl-2-(2H-1,2,3-triazol-2-yl)phenyl]methanone] has been granted marketing authorisation (Kishi et al., PLoS One, 2015; 10(8):e0136910). The sleep-inducing effects of dual orexin receptor antagonists are predominantly mediated via OX2R (Bonaventure et al., J. Pharmacol. Exp. Ther., March 2015, 352, 3, 590-601), whereas the other physiological states such as emotion and reward, cognition, impulse control, regulation of autonomic and neuroendocrine functions, arousal, and vigilance are rather mediated via OX1R.

Due to their sleep-inducing effects, dual OX1R and OX2R antagonists are not suitable for treating disorders related to impulse control deficits as seen in addictions such as substance use disorders, personality disorders, such as borderline personality disorder, eating disorders such as binge eating disorder or attention deficit hyperactivity disorder. Therefore, it is desirable to provide an OX1R selective antagonist for the treatment of impulse control deficits.

Orexin receptor antagonists of various structural classes are reviewed in Roecker et al. (J. Med. Chem. 2015, 59, 504-530). WO03/051872, WO2013/187466, WO2016/034882 and Bioorganic & Medicinal Chemistry 2015, 23, 1260-1275 describe orexin receptor antagonists.

DETAILED DESCRIPTION OF THE INVENTION

The present invention provides novel N-[(Pyrimidinylamino)propanyl]-, N-[(Pyridylamino)propanyl]- and N-[(Pyrazinylamino)propanyl]arylcarboxamide derivatives that unexpectedly are highly potent OX1R antagonists (assay A) further characterized by
1) high selectivity over the OX2 receptor (assay B),
2) a medium to high stability in human liver microsomes (assay C), and
3) no or low MDCK (Madin-Darby canine kidney) efflux (assay D).

Compounds of the present invention are superior to those disclosed in the prior art in terms of the combination of the following key pharmacodynamic and pharmacokinetic parameters:
1) potency as OX1R antagonists,
2) selectivity over the OX2 receptor,
3) stability in human liver microsomes, and
4) MDCK efflux.

Stability in human liver microsomes refers to the susceptibility of compounds to biotransformation in the context of selecting and/or designing drugs with favorable pharmacokinetic properties. The primary site of metabolism for many drugs is the liver. Human liver microsomes contain the cytochrome P450s (CYPs), and thus represent a model system for studying drug metabolization in vitro. Enhanced stability in human liver microsomes is associated with several advantages, including increased bioavailability and longer half-life, which can enable lower and less frequent dosing of patients. Thus, enhanced stability in human liver microsomes is a favorable characteristic for compounds that are to be used for drugs.

The MDCK assay provides information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction. The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1 P-gp. Identical or similar permeabilities in both transport directions indicate passive permeation, vectorial permeability points to additional active transport mechanisms. Higher PEBA than PEAB (PEBA/PEAB>5) indicates the involvement of active efflux mediated by MDR1 P-gp, which might compromises the goal to achieve sufficient brain exposure. Therefore this assay provides valuable support for selection of compounds applicable for further in vivo testing. High permeability not limited by efflux at the blood brain barrier is a favourable characteristic for compounds that are to be used for drugs acting primarily in the CNS Compounds of the present invention differ structurally from Examples 91, 84, 40, 73, 46 and 14 in WO2016/034882 (the closest prior art compounds) in that they contain a central N-ethyl-(propan-2-yl)amino, N-cyclopropylmethyl-(propan-2-yl)amino and N-(2-fluoroethyl)-(propan-2-yl)amino moiety in place of the N-methyl-[butan-2-yl]amino, N-ethyl-[butan-2-yl]amino or N-methyl-[propan-2-yl]amino moiety. These structural differences unexpectedly result in a superior combination of the following key pharmacodynamic and pharmacokinetic parameters:

1) potency as OX1R antagonists,
2) selectivity over the OX2 receptor,
3) stability in human liver microsomes, and
4) MDCK efflux.

Due to their high potency at OX1R and selectivity over OX2R, compounds of the present invention are expected to be both efficacious in in vivo models and to have a sufficient window between efficacy and undesired effects such as drowsiness or sleep.

Due to the superior combination of the key pharmacodynamic and pharmacokinetic parameters (#1-4) compounds of the present invention are expected to demonstrate adequate brain exposure and to have a medium to low in vivo clearance and thus a longer duration of action and higher tolerability. Consequently, compounds of the present invention must be more viable for human use.

General Definitions

Terms not specifically defined herein should be given the meanings that would be given to them by one skilled in the art in light of the disclosure and the context.

Stereochemistry:

Unless specifically indicated, throughout the specification and the appended claims, a given chemical formula or name shall encompass tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt with an acid. Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

Biological Assays

Abbreviations

IP1 D-Myo-Inositol-1-phosphate
IP3 D-myo-inositol-1,4,5-triphosphate
HEPES 4-(2-hydroxyethyl)-1-piperazineethanesulfonic acid
HBSS Hanks' Balanced Salt Solution
BSA bovine serum albumin
DMSO dimethyl sulfoxide
CHO Chinese hamster ovary Activation of the orexin receptors expressed in cell lines results in an increase in intracellular IP3 concentration. IP1, a downstream metabolite of IP3, accumulates in cells following receptor activation and is stable in the presence of LiCl. Using Homogeneous Time-Resolved Fluorescence technology with Lumi4-Tb cryptate (commercially available from Cisbio Bioassay.) and a suitable fluorescence plate reader. This functional response is detectable and quantifiable as described in Trinquet et al. Anal. Biochem. 2006, 358, 126-135, Degorce et al. Curr. Chem. Genomics 2009, 3, 22-32. This technique is used to characterize pharmacological modification of the orexin receptors.

The biological activity of compounds is determined by the following methods:

A. In Vitro Testing of OX1R Potency: OX1R IP1

IP1 measurements are performed in CHO-K1 cells stably expressing the full-length human Orexin 1 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx1 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is re-suspended in medium and then distributed into the assay plates with a density of 10000 cells/25 µL per well. The plates are incubated for one hour at room temperature to reduce edge effects before they are incubated for 24 hours at 37° C./5% $CO_2$. Compounds are prepared by an 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 µL assay buffer (20 µL buffer remained in the wells after washing), followed by adding 5 µL per well of compounds diluted in assay buffer. After 15 minutes of incubation at room temperature 5 µL per well of Orexin A peptide (final concentration: 0.5 nM, and/or 50 nM) dissolved in assay buffer is added to the assay plate. The assay plate is incubated for 60 minutes at 37° C. Then 5 µl per well of Anti-IP1-Cryptate Tb solution and 5 µl per well of IP1-d2 dilution are added and the plate is incubated for a further 60 minutes light protected at room temperature. The emissions at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

B. In Vitro Testing of OX2R Potency: OX2R IP1

IP1 measurements are performed in CHO-K1 cells stably expressing the full-length human orexin 2 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx2 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is resuspended in medium and then distributed into the assay plates with a density of 5000 cells/25 μL per well. The plates are incubated for one hour at room temperature to reduce edge effects before they are incubated for 24 hours at 37° C./5% $CO_2$. Compounds are prepared by a 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay. On the day of the assay, cells in the plate are washed twice with 60 μL assay buffer (20 μL buffer remained in the wells after washing), followed by adding 5 μL per well of compounds diluted in assay buffer. After 15 minutes of incubation at room temperature 5 μL per well of Orexin A peptide (final concentration: 0.5 nM) dissolved in assay buffer is added to the assay plate. The assay plate is incubated for 60 minutes at 37° C. Then 5 μl per well of Anti-IP1-Cryptate Tb solution and 5 μl per well of IP1-d2 dilution are added to all well of the plate and the plate is incubated for a further 60 minutes light protected at room temperature. The emission at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

Kb values from Assay A (OX1R) and Assay B (OX2R) can then provide a selectivity ratio which is independent of the agonist (Orexin A) concentration.

C. Assessment of Metabolic Stability in Human Liver Microsomes (Human MST)

The metabolic stability of the compounds according to the invention may be investigated as follows:

The metabolic degradation of the test compound is assayed at 37° C. with pooled human liver microsomes. The final incubation volume of 100 μL per time point contains TRIS buffer pH 7.6 at room temperature (0.1 M), $MgCl_2$ (5 mM), microsomal protein (1 mg/mL) and the test compound at a final concentration of 1 μM. Following a short pre-incubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life ($t_{1/2}$) is determined by the slope of the semi-logarithmic plot of the concentration-time profile.

D. Assessment of Efflux in Madin-Darby Canine Kidney (MDCK) Cells Transfected with the Human MDR1 Gene Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable.

MDCK-MDR1 cells (1-2×10e5 cells/1 cm2 area) are seeded on filter inserts (Costar transwell polycarbonate or PET filters, 0.4 μm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4 \times H2O$, 15 mM HEPES, 20 mM glucose, 0.25% BSA, pH 7.4) to prepare the transport solutions (0.1-300 μM compound, final DMSO<=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Biological Data

TABLE 1

In vitro potencies of the structurally closest prior art compounds (Example 91, 84, 40, 73, 46, and 14) in WO2016/034882 as reported therein:

| Structure | As described in WO2016/034882 (Table 1, Table 2, Table 3, page177-180) | | |
|---|---|---|---|
| Example # in WO2016/034882 | OX1R | OX2R | OX2R $IC_{50}$/ OX1R $IC_{50}$ |
| Example 91 | Table 1 and 2: not reported Table 3: $pIC_{50}$ = 7.6 corresponds to $IC_{50}$ = 25 nM | Table 1 and 2: not reported Table 3: $pIC_{50}$ <5.1 corresponds to $IC_{50}$ = 7590 nM | Table 3: 318 |
| Example 84 | Table 1 and 2: not reported Table 3: $pIC_{50}$ = 8.7 corresponds to $IC_{50}$ = 1.9 nM | Table 1 and 2: not reported Table 3: $pIC_{50}$ = 6.0 corresponds to $IC_{50}$ = 1000 nM | Table 3: 526 |
| Example 40 | Table 1: $pIC_{50}$ = 7.8 corresponds to $IC_{50}$ = 16 nM Table 2 and 3: not responded | Table 1: $pIC_{50}$ = 5.6 corresponds to $IC_{50}$ = 2500 nM Table 2 and 3: not responded | Table 1: 156 |
| Example 73 | Table 1 and 2: not reported Table 3: $pIC_{50}$ = 8.8 corresponds to $IC_{50}$ = 1.6 nM | Table 1 and 2: not reported Table 3: $pIC_{50}$ <6.0 corresponds to $IC_{50}$ >1000 nM | Table 3: >625 |

TABLE 1-continued

In vitro potencies of the structurally closest prior art compounds (Example 91, 84, 40, 73, 46, and 14) in WO2016/034882 as reported therein:

| Structure | As described in WO2016/034882 (Table 1, Table 2, Table 3, page177-180) | | |
|---|---|---|---|
| Example # in WO2016/034882 | OX1R | OX2R | OX2R $IC_{50}$/ OX1R $IC_{50}$ |
| Example 46 | Table 1: $pIC_{50}$ = 7.7 corresponds to $IC_{50}$ = 20 nM Table 2: $pIC_{50}$ = 2.5 corresponds to $IC_{50}$ = 32 nM Table 3: $pIC_{50}$ = 8.5 corresponds to $IC_{50}$ = 3.2 nM | Table 1: $pIC_{50}$ = 5.1 corresponds to $IC_{50}$ = 7800 nM Table 2: $pIC_{50}$ <5.0 corresponds to $IC_{50}$ >10000 nM Table 3: $pIC_{50}$ <5.0 corresponds to $IC_{50}$ = 10000 nM | Table 1: 390 Table 2: >312 Table 3: 3200 |
| Example 14 | Table 1: $pIC_{50}$ = 8.3 corresponds to $IC_{50}$ = 5.0 nM Table 2: $pIC_{50}$ = 7.8 corresponds to $IC_{50}$ = 16 nM Table 3: not reported | Table 1: $pIC_{50}$ = 6.8 corresponds to $IC_{50}$ = 158 nM Table 2: $pIC_{50}$ = 7.2 corresponds to $IC_{50}$ = 63 nM Table 3: not reported | Table 1: 32 Table 2: 4 |

Compounds of the Present Invention

A full and detailed comparison of the key biological properties (including OX1R and OX2R potencies, stability in human liver microsomes and MDCK efflux) of all compounds of the present invention with the corresponding closest prior art compounds in WO2016/034882 respectively is shown in Table 1.

Examples 1, 2 and 3 of the present invention differ structurally from Example 91 in WO2016/034882 i.e. the closest prior art compound in that it contain a central N-cyclopropylmethyl-(propan-2-yl)amino moiety (Example 1), N-fluoroethyl-(propan-2-yl)amino moiety (Example 2) and N-ethyl-(propan-2-yl)amino moiety (Example 3) in place of the N-methyl-[butan-2-yl]amino moiety. Furthermore, Examples 1 and 2 contain a fluorine atom in a different position at the phenyl ring while Example 3 contains a chlorine atom in a different position of the phenyl ring. These structural differences unexpectedly result in Examples 1, 2 and 3 being more potent at OX1R and more selective while being still in an acceptable range with regard to metabolic stability and MDCK efflux when compared to Example 91 in WO2016/034882.

Examples 4, 5, 6 and 7 of the present invention differ structurally from Example 91 in WO2016/034882 i.e. the closest prior art compound in that it contain a central N-ethyl-(propan-2-yl)amino moiety in place of the N-methyl-[butan-2-yl]amino moiety. They are characterized by additional structural features thereby differing structurally farther from Example 91 in WO2016/034882 in that the phenyl group carries one or two fluorine atoms with a different substitution pattern. Examples 4, 5 and 6 have a further structural difference when compared to Example 91 in WO2016/034882, i.e. a bromo or chloro substituted pyrimidine instead of a trifluoromethyl substituted pyrimidine, while Example 7 contains a differently substituted pyridine in place of trifluoromethylpyrimidine. These structural differences unexpectedly result in a significantly higher potency and selectivity in conjunction with adequate in vitro pharmacokinetic properties when compared to Example 84 in WO2016/034882.

Example 8 of the present invention differs structurally from Example 84 in WO2016/034882, i.e. the closest prior art compound in that it contains a central N-ethyl-(propan-2-yl)amino moiety in place of the N-methyl-[butan-2-yl] amino moiety and a substituted phenyl ring with two fluorine atoms instead of a methyl-substituted pyridyl ring. These structural differences unexpectedly result in Example 8 demonstrating an over 150-fold higher potency, a 7-fold higher selectivity and significantly better stability in human liver microsomes and low MDCK efflux when compared to Example 84 in WO2016/034882.

Example 9 of the present invention differs structurally from Example 84 in WO2016/034882, i.e. the closest prior art compound in that it contains a central N-methyl-(propan-2-yl)amino moiety in place of the N-methyl-[butan-2-yl] amino moiety and a fluorine-substituted phenyl ring instead of a methyl-substituted pyridyl ring. These structural differences unexpectedly result in Example 9 demonstrating a nearly 10-fold higher potency, a higher selectivity and significantly better stability in human liver microsomes and low MDCK efflux when compared to Example 84 in WO2016/034882.

Example 10 of the present invention differs structurally from Example 40 in WO2016/034882, the closest prior art compound in that it contains a central N-ethyl-(propan-2-yl)amino moiety in place of the N-methyl-[butan-2-yl]amino moiety. Unexpectedly, this structural difference results in 16-fold better potency, better selectivity, significantly better stability in human liver microsomes with comparable MDCK efflux when compared to Example 40 in WO2016/034882.

Examples 11 and 12 of the present invention differ structurally from Examples 46 and 73 in WO2016/034882, i.e. the closest prior art compounds in that they contain a central N-ethyl-(propan-2-yl)amino moiety in place of the N-methyl-[butan-2-yl]amino moiety and N-ethyl-[butan-2-yl]amino moiety, respectively. Examples 11 and 12 differ structurally farther from Examples 46 and 73 in WO2016/034882 in that the pyridine nitrogen is positioned differently and that the pyridine moiety is substituted with a chlorine (Example 11) and fluorine (Example 12) instead of a methyl group. These structural differences unexpectedly result in Examples 11 and 12 demonstrating a >10 fold higher potency along with better selectivity and adequate pharmacokinetic properties when compared to Example 46 in WO2016/034882. Examples 11 and 12 are superior to Example 73 in WO2016/034882 as well in that they possess an approximately 2-fold higher potency, comparable MDCK efflux and significantly improved stability in human liver microsomes (Example 11).

Example 13 of the present invention differ structurally from Example 14 in WO2016/034882, i.e. the closest prior art compound in that it contains a central N-ethyl-(propan-2-yl)amino moiety in place of the N-methyl-(propan-2-yl) amino moiety. Furthermore, it contains a bromopyrimidyl group instead of a chloropyridyl group and a methylpyrimidyl moiety instead of a phenyl moiety. Unexpectedly, Example 13 is of higher potency and selectivity and markedly higher stability (in human liver microsomes) than Example 14 in WO2016/034882.

These results demonstrate that compounds of the present invention unexpectedly are more potent OX1R antagonists and more selective over the OX2 receptor than the structurally most similar examples disclosed in WO2016/034882 (closest prior art compounds) respectively.

Results in Table 2 show that, when compared to any of the prior art compounds according to Examples 14, 40, 46, 73, 84 and 91 in WO2016/034882, compounds of the present invention unexpectedly are superior in at least one of the following key pharmacodynamic and pharmacokinetic parameters including potency, selectivity, stability in human liver microsomes and MDCK efflux.

TABLE 2

Comparison of biological data of the compounds of the present invention with the closest prior art compounds in WO2016/034882

| Example | Structure | Assay 1 OX1R Kb [nM] (Orexin A concentration) | Assay B OX2R Kb [nM] (0.5 nM Orexin A concentration) | OX2R Kb/ OX1R Kb | Assay C: Human MST $t_{1/2}$ [min] | Assay D: MDC Kefflux ratio (BA/AB) |
|---|---|---|---|---|---|---|
| Ex 91 in WO2016/034882 | 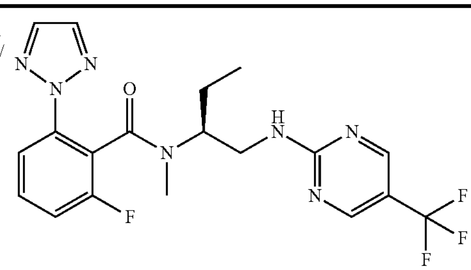 | 3.63 (0.5 nM) | 313 | 86 | >130 | <3 |
| 1 | 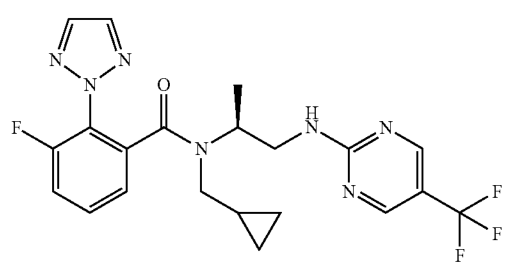 [SMILES: C[C@@H](CNc1ncc(C(F)(F)F)cn1)N(CC1CC1)C(=O)c1cccc(F)c1-n1nccn1] | 0.214 (50 nM) | 34.8 | 163 | 73 | <3 |
| 2 | 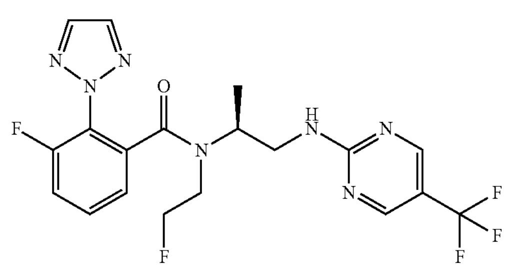 [SMILES: C[C@@H](CNc1ncc(C(F)(F)F)cn1)N(CCF)C(=O)c1cccc(F)c1-n1nccn1] | 0.670 (50 nM) | 104 | 155 | >130 | <3 |

TABLE 2-continued

Comparison of biological data of the compounds of the present invention with the closest prior art compounds in WO2016/034882

| Example | Structure | Assay 1 OX1R Kb [nM] (Orexin A concentration) | Assay B OX2R Kb [nM] (0.5 nM Orexin A concentration) | OX2R Kb/ OX1R Kb | Assay C: Human MST $t_{1/2}$ [min] | Assay D: MDC Kefflux ratio (BA/AB) |
|---|---|---|---|---|---|---|
| 3 | 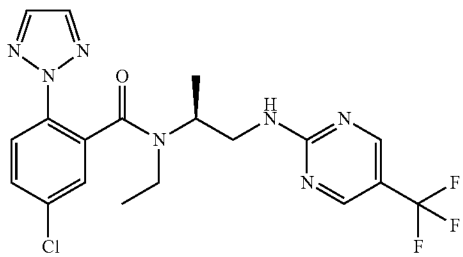 [SMILES: CCN(C(=O)c1cc(Cl)ccc1-n1nccn1)[C@@H](C)CNc1ncc(C(F)(F)F)cn1] | 0.032 (50 nM) | 10.1 | 316 | 130 | <3 |
| 4 | 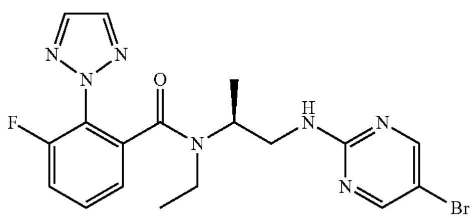 [SMILES: CCN(C(=O)c1cccc(F)c1-n1nccn1)[C@@H](C)CNc1ncc(Br)cn1] | 0.116 (50 nM) | 24.4 | 210 | >130 | <3 |
| 5 | 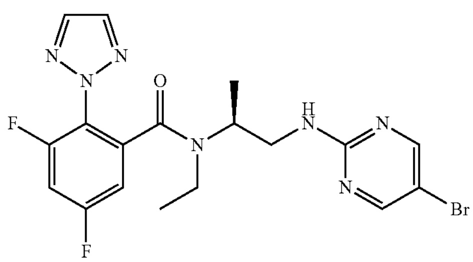 [SMILES: CCN(C(=O)c1cc(F)cc(F)c1-n1nccn1)[C@@H](C)CNc1ncc(Br)cn1] | 0.184 (50 nM) | 42.1 | 229 | >130 | <3 |
| 6 | 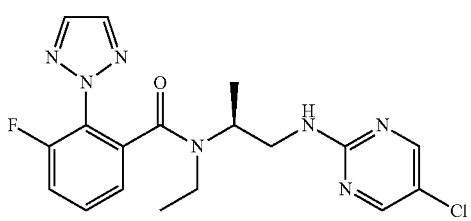 [SMILES: CCN(C(=O)c1cccc(F)c1-n1nccn1)[C@@H](C)CNc1ncc(Cl)cn1] | 0.210 (50 nM) | 26.3 | 125 | >130 | <3 |
| 7 | 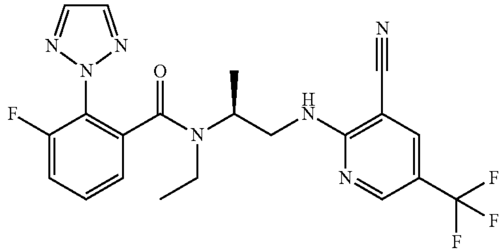 [SMILES: CCN(C(=O)c1cccc(F)c1-n1nccn1)[C@@H](C)CNc1ncc(C(F)(F)F)cc1C#N] | 0.021 (50 nM) | 20.4 | 971 | 89 | <3 |

TABLE 2-continued
Comparison of biological data of the compounds of the present invention with the closest prior art compounds in WO2016/034882
| Example | Structure | Assay 1 OX1R Kb [nM] (Orexin A concentration) | Assay B OX2R Kb [nM] (0.5 nM Orexin A concentration) | OX2R Kb/ OX1R Kb | Assay C: Human MST $t_{1/2}$ [min] | Assay D: MDC Kefflux ratio (BA/AB) |
|---|---|---|---|---|---|---|
| Ex 84 in WO2016/034882 | 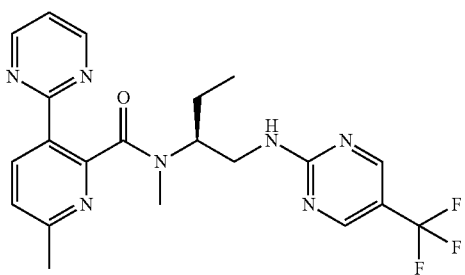 [SMILES: CC[C@@H](CNc1ncc(C(F)(F)F)cn1)N(C)C(=O)c1nc(C)ccc1-c1ncccn1] | 2.20 (50 nM) | 229 | 104 | 41 | <3 |
| 8 | 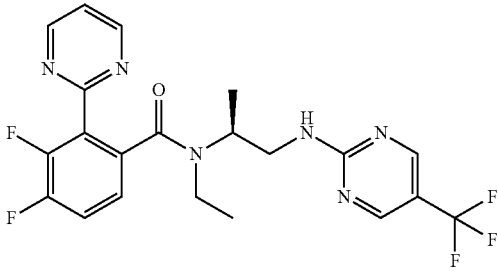 [SMILES: CCN(C(=O)c1ccc(F)c(F)c1-c1ncccn1)[C@@H](C)CNc1ncc(C(F)(F)F)cn1] | 0.014 (50 nM) | 10.3 | 736 | >130 | <3 |
| 9 | 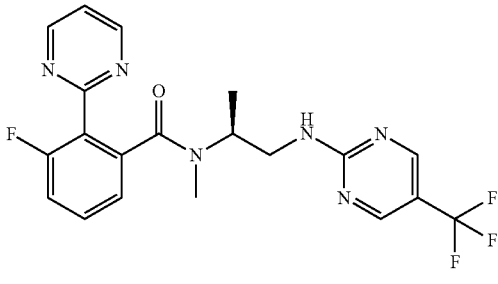 [SMILES: C[C@@H](CNc1ncc(C(F)(F)F)cn1)N(C)C(=O)c1cccc(F)c1-c1ncccn1] | 0.223 (50 nM) | 51.5 | 231 | >130 | <3 |
| Ex 40 in WO2016/034882 | 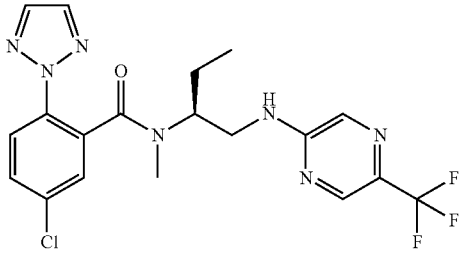 [SMILES: CC[C@@H](CNc1cnc(C(F)(F)F)cn1)N(C)C(=O)c1cc(Cl)ccc1-n1nccn1] | 0.180 (50 nM) | 38 | 211 | 9 | <3 |
| 10 | 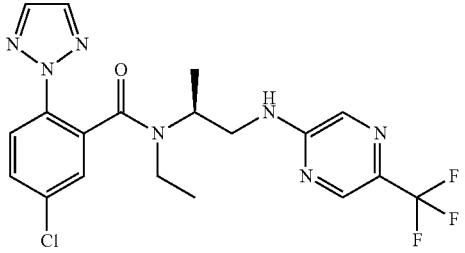 [SMILES: CCN(C(=O)c1cc(Cl)ccc1-n1nccn1)[C@@H](C)CNc1cnc(C(F)(F)F)cn1] | 0.011 (50 nM) | 4.1 | 373 | 130 | <3 |

TABLE 2-continued

Comparison of biological data of the compounds of the present invention with the closest prior art compounds in WO2016/034882

| Example | Structure | Assay 1 OX1R Kb [nM] (Orexin A concentration) | Assay B OX2R Kb [nM] (0.5 nM Orexin A concentration) | OX2R Kb/ OX1R Kb | Assay C: Human MST $t_{1/2}$ [min] | Assay D: MDC Kefflux ratio (BA/AB) |
|---|---|---|---|---|---|---|
| Ex 73 in WO2016/034882 | 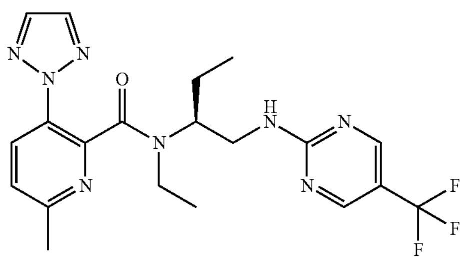 [SMILES: CC[C@@H](CNc1ncc(C(F)(F)F)cn1)N(CC)C(=O)c1nc(C)ccc1-n1nccn1] | 0.309 (50 nM) | 145 | 469 | 11 | <3 |
| Ex 46 in WO2016/034882 | 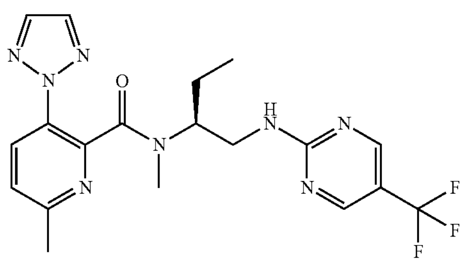 [SMILES: CC[C@@H](CNc1ncc(C(F)(F)F)cn1)N(C)C(=O)c1nc(C)ccc1-n1nccn1] | 1.558 (50 nM) | 372 | 240 | 32 | <3 |
| 11 | 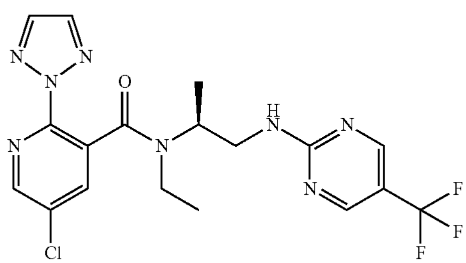 | 0.166 (50 nM) | 167 | 1006 | >130 | <3 |
| 12 | 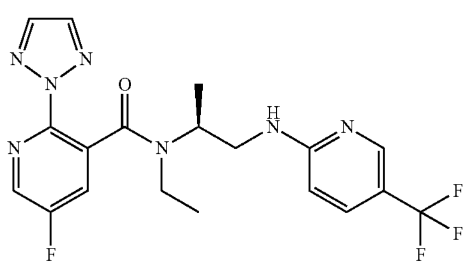 [SMILES: CCN(C(=O)c1cc(F)cnc1-n1nccn1)[C@@H](C)CNc1ccc(C(F)(F)F)cn1] | 0.156 (50 nM) | 117 | 750 | 44 | 3-5.5 |
| Ex 41 in WO2016/034882 | 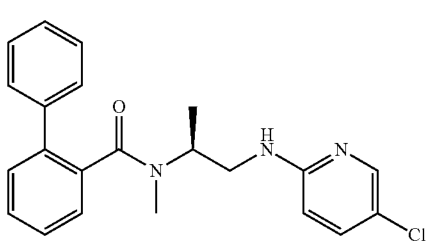 [SMILES: C[C@@H](CNc1ccc(Cl)cn1)N(C)C(=O)c1ccccc1-c1ccccc1] | 0.171 (50 nM) | 4.7 | 27 | 2 | <3 |

TABLE 2-continued

Comparison of biological data of the compounds of the present invention with the closest prior art compounds in WO2016/034882

| Example | Structure | Assay 1 OX1R Kb [nM] (Orexin A concentration) | Assay B OX2R Kb [nM] (0.5 nM Orexin A concentration) | OX2R Kb/ OX1R Kb | Assay C: Human MST $t_{1/2}$ [min] | Assay D: MDC Kefflux ratio (BA/AB) |
|---|---|---|---|---|---|---|
| 13 | 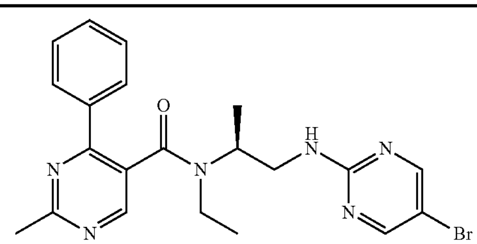 | 0.089 (50 nM) | 68.3 | 767 | 76 | <3 |

Use in Treatment/Method of Use

The present invention is directed to compounds which are useful in the treatment of a disease, disorder and condition wherein the antagonisms of OX1R is of therapeutic benefit, including but not limited to the treatment and/or prevention of psychiatric and neurological conditions associated with impulse control deficits. Such impulse control deficits are seen in addictions including substance use disorders; personality disorders such as borderline personality disorder; eating disorders such as binge eating disorder; or attention deficit hyperactivity disorder. According to a further aspect of the invention, compounds of the present invention are useful in the treatment of OX1R related pathophysiological disturbances in arousal/wakefulness, appetite/food intake, cognition, motivated behaviours/reward, mood and stress.

In view of their pharmacological effect, compounds of the present invention are suitable for use in the treatment of a disease or condition selected from the list consisting of (1) treatment or prevention of substance abuse/dependence/seeking or addiction as well as relapse prevention (including but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics, (2) eating disorders, such as binge eating, bulimia nervosa, anorexia nervosa, other specified feeding or eating disorders, obesity, overweight, cachexia, appetite/taste disorders, vomiting, nausea, Prader-Willi-Syndrome, hyperphagia, appetite/taste disorders, (3) attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la Tourette's syndrome, restless legs syndrome, dementia, dyskinesia, severe mental retardation, neurodegenerative disorders including nosological entities such as disinhibition-dementia-parkinsonism-amyotrophy complex, pallido-ponto-nigral degeneration, (4) cognitive dysfunction in psychiatric or neurological disorder, cognitive impairments associated with schizophrenia, Alzheimer's disease and other neurological and psychiatric disorders, (5) mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder, (6) sexual disorder, sexual dysfunction, psychosexual disorder, (7) impulse control disorders such as pathological gambling, trichotillomania, intermittent explosive disorder, kleptomania, pyromania, compulsive shopping, internet addiction, sexual compulsion, (8) sleep disorders such as narcolepsy, jetlag, sleep apnea, insomnia, parasomnia, disturbed biological and circadian rhythms, sleep disturbances associated with psychiatric and neurological disorders, (9) treatment, prevention and relapse control of impulsivity and/or impulse control deficits and/or behavioural disinhibition in any psychiatric and/or neurological condition,

(10) personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders

(11) neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Combination Therapy

Compounds according to the present invention can be combined with other treatment options known to be used in the art in connection with a treatment of any of the indications the treatment of which is in the focus of the present invention.

Among such treatment options that are considered suitable for combination with the treatment according to the present inventions are:
- Antidepressants
- Mood stabilizers
- Antipsychotics
- Anxiolytics
- Antiepileptic drugs
- Sleeping agents
- Cognitive enhancer
- Stimulants
- Non-stimulant medication for attention deficit hyperactivity disorder
- Additional psychoactive drugs.

EXPERIMENTAL SECTION

List of Abbreviations

RT room temperature
ESI-MS electrospray ionisation mass spectrometry
APCI atmospheric pressure chemical ionization
aq. aqueous
MS mass spectrometry
MeOH methanol
EtOH ethanol
EA ethyl acetate
DMF N,N-dimethylformamide
DCM dichloromethane
DMA dimethylacetamide
TEA triethylamine
THF tetrahydrofuran
dppf 1,1'-bis(diphenylphosphanyl)ferrocene
DIPEA N,N-diisopropylethylamine
HATU 1-[bis(dimethylamino)methylene]-1H-1,2,3-triazolo[4,5-b]pyridinium 3-oxid hexafluorophosphate
DBU 1,8-Diazabicyclo[5.4.0]undec-7-ene
DIAD diisopropyl azodicarboxylate
Rt retention time
h hour(s)
min minutes
sat. saturated
ACN acetonitrile
TFA trifluoroacetic acid
HPLC high-performance liquid chromatography
HPLC-MS high-performance liquid chromatography-mass spectrometry
CIP 2-chloro-4,5-dihydro-1,3-dimethyl-1H-imidazolium hexafluorophosphate
TLC thin layer chromatography HPLC-Methods:

Method Name: A
Column: Venusil XBP-C18, 2.1×50 mm, 5 μm
Column Supplier: Agela Technologies

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 90 | 10 | 0.8 | 50 |
| 0.40 | 90 | 10 | 0.8 | 50 |
| 3.40 | 0 | 100 | 0.8 | 50 |
| 3.85 | 0 | 100 | 0.8 | 50 |
| 3.86 | 90 | 10 | 0.8 | 50 |
| 4.50 | 90 | 10 | 0.8 | 50 |

Method Name: B
Column: Chromolith Flash RP-18e 25-2 mm
Column Supplier: Merck

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 95 | 5 | 1.5 | 40 |
| 0.70 | 5 | 95 | 1.5 | 40 |
| 1.15 | 5 | 95 | 1.5 | 40 |
| 1.16 | 95 | 5 | 1.5 | 40 |
| 1.60 | 5 | 95 | 1.5 | 40 |

Method Name: C
Column: XBridge C18, 4.6×30 mm, 3.5 μm
Column Supplier: Waters

| Gradient/Solvent Time [min] | % Sol [H2O, 0.1% NH3] | % Sol [ACN] | Flow [mL/min] | Temp [° C.] |
|---|---|---|---|---|
| 0.00 | 97 | 3 | 5 | 60 |
| 0.02 | 97 | 3 | 5 | 60 |
| 1.60 | 0 | 100 | 5 | 60 |
| 1.70 | 0 | 100 | 5 | 60 |

Method Name: D
Column: XBridge C18, 3×30 mm, 2.5 μm
Column Supplier: Waters

| Gradient/Solvent Time [min] | % Sol [H2O, 0.1% NH3] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: E
Column: Xselect CSH, 2.5 μm, 4.6×50 mm/Column Supplier: Waters

| Gradient/Solvent Time [min] | % Sol [90% H$_2$O + 10% ACN + 0.1% HCOOH] | % Sol [90% ACN + 10% H$_2$O + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |

-continued

| Gradient/ Solvent Time [min] | % Sol [90% H$_2$O + 10% ACN + 0.1% HCOOH] | % Sol [90% ACN + 10% H$_2$O + 0.1% HCOOH] | Flow [mL/min] | Temp [° C.] |
|---|---|---|---|---|
| 5.50 | 100 | 0 | 1.4 | RT |
| 6.00 | 100 | 0 | 1.4 | RT |

Method Name: F
  Column: Xselect CSH Phenyl-Hexyl, 2.5 μm, 4.6×50 mm/
  Column Supplier: Waters

| Gradient/ Solvent Time [min] | % Sol [90% H$_2$O + 10% ACN + 0.1% HCOOH] | % Sol [90% ACN + 10% H$_2$O + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

Method Name: G
  Column: Synergi Hydro RP100A, 2.5 μm, 3×50 mm
  Column Supplier: Phenomenex

| Gradient/ Solvent Time [min] | % Sol [90% H$_2$O + 10% ACN + 5 mM NH$_4$COOH] | % Sol [90% ACN + 10% H$_2$O] | Flow [mL/min] | Temp [° C.] |
|---|---|---|---|---|
| 0.00 | 100 | 0 | 1.2 | RT |
| 4.00 | 0 | 100 | 1.2 | RT |
| 5.30 | 0 | 100 | 1.2 | RT |
| 5.50 | 100 | 0 | 1.2 | RT |
| 6.00 | 100 | 0 | 1.2 | RT |

Method Name: H
  Column: HSS C18, 1.8 μm, 2.1×50 mm
  Column Supplier: Waters

| Gradient/Solvent Time [min] | % Sol [90% H$_2$O + 10% ACN + 0.1% CF$_3$COOH] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: I
  Column: BEH C18 1.7 μm 2.1×50 mm
  Column Supplier: Waters

| Gradient/ Solvent Time [min] | % Sol [90% H$_2$O + 10% ACN + NH$_4$COOH 5 mM] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: J
  Column: XBridge C18 2.5 μm, 3.0*30 mm
  Column Supplier: Waters

| Gradient/Solvent Time [min] | % Sol [Water 0.1% NH3] | % Sol [Acetonitrile] | Flow [mL/min] | Temp [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Method Name: K
  Column: Sunfire, 3×30 mm, 2.5 μm
  Column Supplier: Waters

| Gradient/Solvent Time [min] | % Sol [H$_2$O, 0.1% TFA] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.00 | 0 | 100 | 2.2 | 60 |
| 1.25 | 0 | 100 | 3 | 60 |
| 1.40 | 0 | 100 | 3 | 60 |

Method Name: L
  Column: Synergi Hydro RP100A, 2.5 μm, 3×50 mm
  Column Supplier: Phenomenex

| Gradient/ Solvent Time [min] | % Sol [90% H$_2$O + 10% ACN + 10 mM NH$_4$COOH] | % Sol [90% ACN + 10% H$_2$O + 10 mM NH$_4$COOH] | Flow [mL/min] | Temp [° C.] |
|---|---|---|---|---|
| 0.00 | 100 | 0 | 1.2 | RT |
| 0.05 | 100 | 0 | 1.2 | RT |
| 6.50 | 0 | 100 | 1.2 | RT |
| 7.50 | 0 | 100 | 1.2 | RT |
| 8.00 | 100 | 0 | 1.2 | RT |
| 9.00 | 100 | 0 | 1.2 | RT |

Method Name: M
  Column: BEH C18 1.7 μm 2.1×50 mm
  Column Supplier: Waters

| Gradient/ Solvent Time [min] | % Sol [90% H$_2$O + 10% ACN + NH$_4$COOH 5 mM] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: N
  Column: BEH C18 1.7 μm 2.1×50 mm
  Column Supplier: Waters

| Gradient/ Solvent Time [min] | % Sol [90% H₂O + 10% ACN + NH₄COOH 5 mM] | % Sol [90% ACN + 10% H₂O] | Flow [mL/min] | Temp [° C.] |
|---|---|---|---|---|
| 0.00 | 100 | 0 | 0.7 | 35 |
| 2.40 | 0 | 100 | 0.7 | 35 |
| 2.70 | 0 | 100 | 0.7 | 35 |
| 2.80 | 100 | 0 | 0.7 | 35 |
| 3.00 | 100 | 0 | 0.7 | 35 |

HPLC traces and NMR spectra of the examples and some advanced intermediates are of increased complexity due to the fact that these compounds exist in an equilibrium of multiple rotameric forms. In the case of multiple peaks in the HPLC spectrum, the retention time of the main peak is reported.

Preparation of Intermediates

Acid Intermediates:

| Acid | Name | Structure | Reference/source |
|---|---|---|---|
| A-1 | 3-Fluoro-2-[1,2,3]triazol-2-yl-benzoic acid | 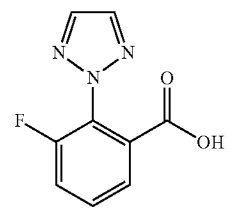 [SMILES: O=C(O)c1cccc(F)c1-n1nccn1] | WO2011/50198, Page 47, Intermediate 5 |
| A-2 | 3,5-Difluoro-2-[1,2,3]triazol-2-yl-benzoic acid | 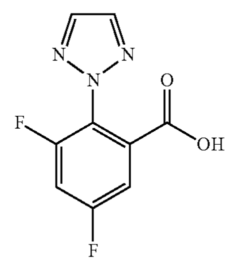 [SMILES: O=C(O)c1cc(F)cc(F)c1-n1nccn1] | WO2011/50198, Page 64, Compound (w); See also in PCT/EP2017/058318 |
| A-3 | 5-Chloro-2-[1,2,3]triazol-2-yl-benzoic acid | 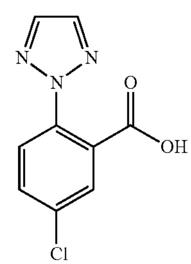 [SMILES: O=C(O)c1cc(Cl)ccc1-n1nccn1] | WO2011/50198, Page 48, Intermediate 9 |
| A-4 | 3-Fluoro-2-pyrimidin-2-yl-benzoic acid | 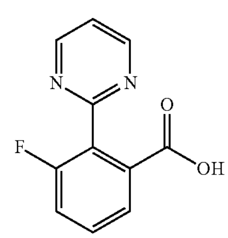 [SMILES: O=C(O)c1cccc(F)c1-c1ncccn1] | WO2011/50200, page 78, Intermediate 52 |
| A-5 | 2-Methyl-4-phenyl-pyrimidine-5-carboxylic acid | 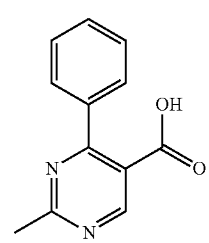 [SMILES: Cc1ncc(C(=O)O)c(-c2ccccc2)n1] | commercially available from Fluorochem catalog number 322095, MDL number: MFCD02682072 |

5-Fluoro-2-[1,2,3]triazol-2-yl-nicotinic Acid A-6

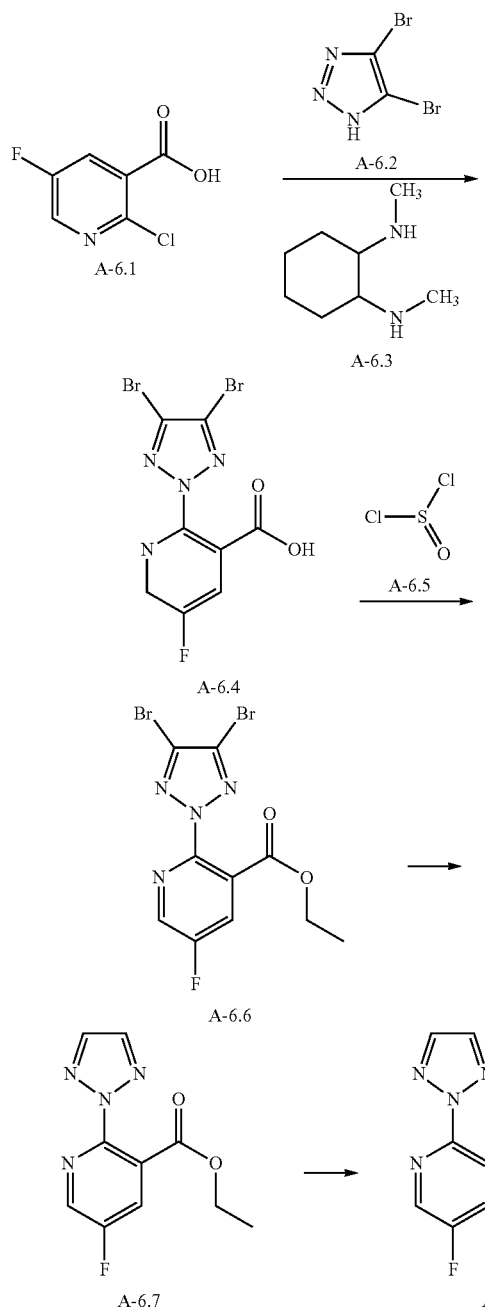

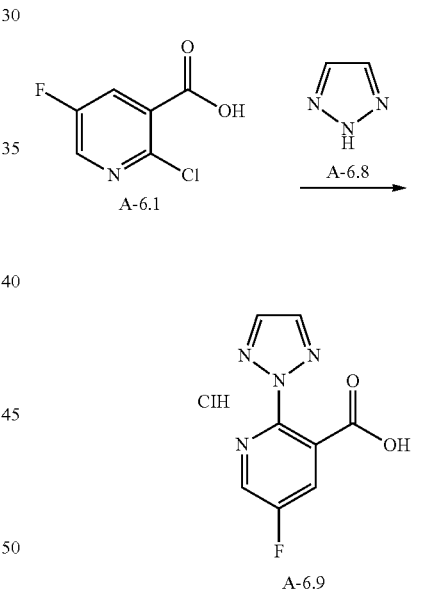

Step 2: To A-6.4 (3.60 g, 7.87 mmol) in anhydrous EtOH (36 mL) is added dropwise A-6.5 (0.86 mL, 11.8 mmol). The mixture is heated to reflux overnight, then concentrated. The crude product is purified by flash column chromatography on silica gel. The so-obtained compound is taken up into DCM and washed with $NaHCO_3$ (sat. solution). The organic phase is dried and concentrated to provide 2.30 g of A-6.6. ES+/−: 395 [M+H]$^+$; HPLC (Rt): 1.23 min (method I).

Step 3: To A-6.6 (2.0 g, 5.0 mmol) dissolved in EtOH (25 mL) is added TEA (1.4 mL, 10 mmol) and palladium on carbon (10%, 0.20 g, 1.88 mmol). The reaction is stirred overnight under an atmosphere of hydrogen (2 bar). The mixture is filtered through a Celite pad and the concentrated. The residue is dissolved in DCM and washed with citric acid (sat. aq. solution). The organic phase is dried and concentrated to afford 1.4 g of A-6.7. ES+/−: 237 [M+H]$^+$; HPLC (Rt): 0.88 min (method I).

Step 4: To a mixture of A-6.7 (0.85 g, 2.52 mmol) in water (5.0 mL) and THF (15 mL) is added LiOH monohydrate (0.32 g, 7.60 mmol) and the mixture is stirred at RT overnight. The mixture is concentrated and the water phase is acidified with HCl (4M aq. solution) and extracted with DCM. The organic phase is dried and concentrated to afford 0.6 g of A-6. ES+/−: 209 [M+H]$^+$; HPLC (Rt): 0.61 min (method H).

Alternative Route for A-6:

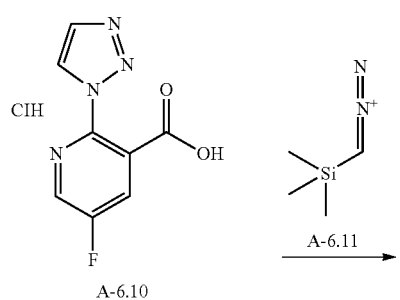

Step 1: A mixture of A-6.1 (2.00 g, 11.0 mmol), A-6.2 (3.88 g, 17.1 mmol), CuI (0.13 g, 0.68 mmol), A-6.3 (0.15 mL, 1.03 mmol) and $K_2CO_3$ (2.36 g, 17.1 mmol) in dry DMF (10 mL) is heated to 120° C. by microwave for 40 min. The mixture is poured into water and extracted with $Et_2O$. The aq. phase is acidified with HCl (4M aq. solution) and extracted with EA. The combined organic phases are dried and concentrated to give the crude product which is purified by flash column chromatography on silica gel (using a solvent gradient from 100% EA to EA/MeOH=9/1) to provide 3.6 g of A-6.4. APCI+/−: 365 [M+H]$^+$; HPLC (Rt): 1.10 min (method G).

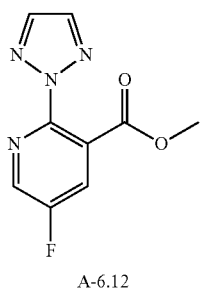

A-6.12

Step 1: A mixture of A-6.1 (15.0 g, 81.0 mmol), A-6.8 (11.0 g, 0.16 mol), CuI (0.94 g, 4.90 mmol) and Cs₂CO₃ (53.0 g, 0.16 mol) in 1,4-dioxane (60 mL) and H₂O (0.50 mL) is heated to 100° C. by microwave for 10 min. The mixture is poured into water and extracted with EA. The organic phase is washed with water and aq. phase is acidified with HCl (5M aq. solution) and extracted with EA. The combined organic phases are washed with brine, dried and concentrated to afford 12 g of a mixture of A-6.9 and A-6.10.

Step 2: The mixture of A-6.9 and A-6.10 (4.0 g, 6.5 mmol) is dissolved in MeOH (50 mL) and A-6.11 is added dropwise to the mixture cooled to 0° C. The reaction is stirred at RT overnight. The mixture is quenched with acetic acid and the product is extracted with EA. The organic phase is washed with water and brine, dried and concentrated. The crude product is purified by preparative HPLC (using a solvent gradient H₂O/ACN with NH₄HCO₃) to afford 2.6 g of A-6.12 as a single isomer. ESI-MS: 223 [M+H]⁺; HPLC (Rt): 0.77 min (method F). The hydrolysis of A-6.12 is carried out in analogy to the conversion of A-6.7 to A-6.

5-Chloro-2-[1,2,3]triazol-2-yl-nicotinic Acid A-7

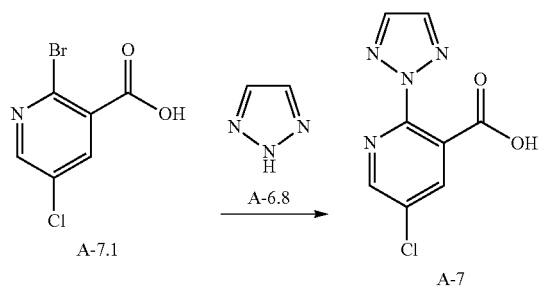

A mixture of A-7.1 (9.50 g, 40.2 mmol), A-6.8 (3.33 g, 48.21 mmol), CuI (0.58 g, 4.02 mmol) and Cs₂CO₃ (14.26 g, 44.20 mmol) in Dioxane (200 mL) and water (10 mL) is heated to 100° C. for 12 h. The mixture is acidified with HCl (0.5 M aq. solution) to pH=2. The mixture is extracted with EA, the organic phase is washed with brine, dried and concentrated to give the crude product 5.0 g of A-7. ESI-MS: 225 [M+H]⁺; TLC (Rf): 0.1 (silica gel; DCM/MeOH 10/1)

3,4-Difluoro-2-pyrimidin-2-yl-benzic Acid A-8

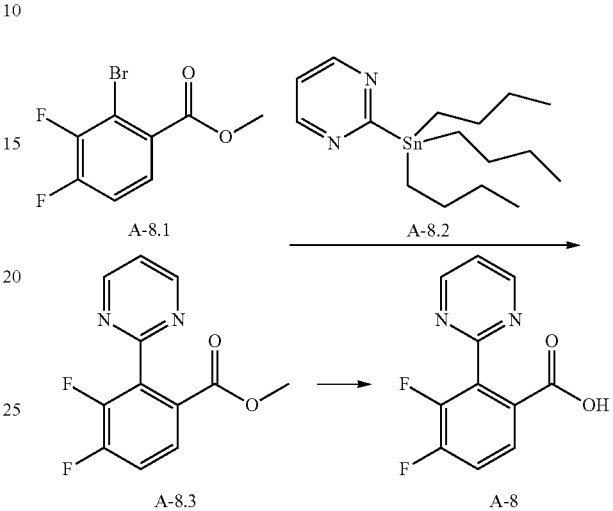

Step 1: To a mixture of A-8.1 (32.0 g, 0.127 mol), A-8.2 (51.76 g, 0.140 mol), CsF (40.42 g, 0.268 mol) and CuI (2.46 g, 0.013 mol) in DMF (400 mL) is added Pd(PPh₃)₄ (15.0 g, 0.013 mol) under a nitrogen atmosphere. The mixture is heated at 120° C. for 16 h. The reaction mixture is poured into NH₄Cl (aq. Solution, 2.0 L) and extracted with EA): The organic layer is dried and concentrated to give the crude product which is purified by flash column chromatography on silica gel (using petroleum ether/EA 10/1-1/1) to provide 16.0 g of A-8.3. TLC (Rf): 0.5 (silica gel; petroleum ether/EA 2/1)

Step 2: A mixture of A-8.3 (16.0 g, 0.064 mol), MeOH (200 mL) and NaOH (7.67 g, 0.192 mol), and H₂O (200 mL) is stirred at RT for 2 h. The mixture is acidified with HCl (aq. solution) to pH=7 and extracted with EA, the organic phase is dried and concentrated to provide 12.0 g of A-8. ESI-MS: 234.0 [M−H]⁻; TLC (Rf): 0.5 (silica gel; DCM/MeOH 3/1)

Synthesis of Amine Intermediates (S)—N*2*-cyclopropylmethyl-N*1*-(5-trifluoromethyl-pyrimidin-2-yl)-propane-1,2-diamine hydrochloride B-1

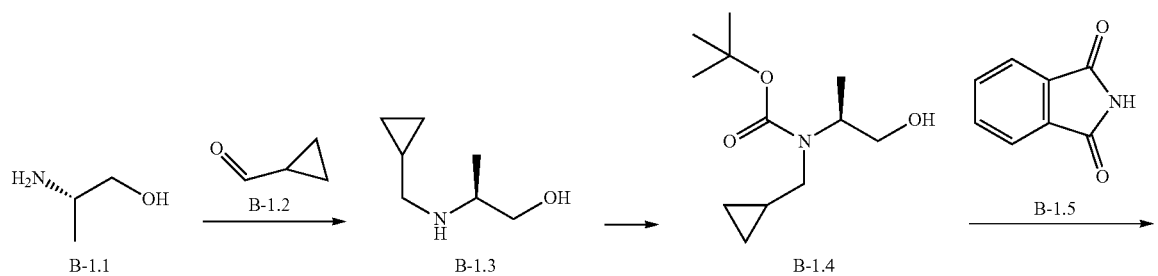

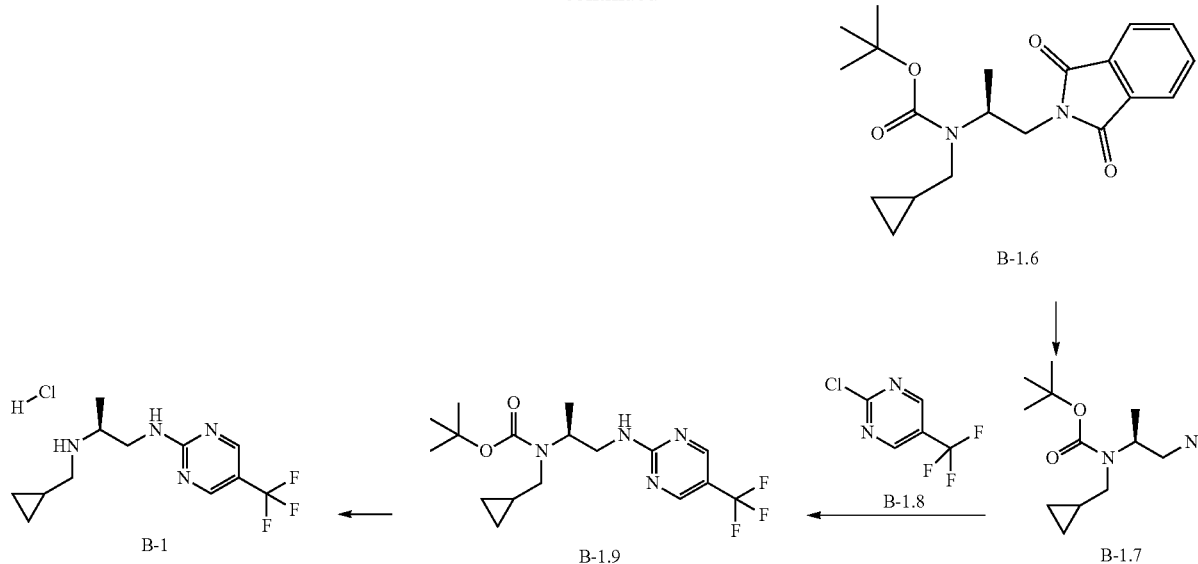

Step 1: To a mixture of B-1.1 (500 mg, 6.66 mmol) in MeOH under nitrogen atmosphere B-1.2 (0.55 mL, 7.36 mmol) is added at RT, then AcOH is added and the reaction mixture is stirred at RT for 5 h. The reaction mixture is cooled and sodium triacetoxyborohydride (2.83 g, 13.35 mmol) is added portionwise at 0° C. and the mixture is warmed to RT overnight. The solvent is evaporated and the residue is treated with aq. NaHCO₃ solution and extracted with DCM. The organic phase is concentrated to get 590.0 mg of B-1.3. ESI-MS: 129 [M+H]⁺; HPLC (Rt): 0.28 min (method M).

Step 2: To a mixture of B-1.3 (380.0 mg, 2.94 mmol) in THF di-tert-butyldicarbonate (700 mg, 3.21 mmol) is added and stirred at RT for 3 h. The reaction mixture is poured into water and extracted with EA. The organic phase is washed with diluted citric acid and concentrated. The crude product is purified by flash column chromatography on silica gel (using a solvent n-hexane/EA 7/3) to afford 500 mg of B-1.4. ESI-MS: 229 [M+H]⁺; HPLC (Rt): 1.03 min (method M).

Step 3: To a mixture of B-1.4 (500 mg, 2.18 mmol), B-1.5 (420 mg, 2.86 mmol) and PPh₃ (740 mg, 2.82 mmol) in dry THF (18 mL) is added DIAD (0.62 mL, 3.43 mmol) at 0° C. and under a nitrogen atmosphere. The mixture is stirred at RT for 16 h. The solvent is concentrated; the residue is treated with H₂O and extracted with EA. The organic layer is separated, dried and concentrated. The residue is purified by flash column chromatography on silica gel (using a solvent mixture of n-hexane/EA 7/1) to get 480 mg of B-1.6. ESI-MS: 358 [M+H]⁺; HPLC (Rt): 1.36 min (method M).

Step 4: Hydrazine hydrate (0.20 mL, 4.0 mmol) is added to B-1.6 (450 mg, 1.26 mmol) in dry EtOH (24 mL) at RT. The mixture is stirred for 20 h, then cooled on an ice bath and the solid is filtered and washed with cold EtOH. The solvent is evaporated and the residue is treated with cold citric acid (10% aq. solution). The mixture is extracted with EA. The organic layer is separated. The water phase is treated with NH₄OH and extracted with EA. The organic layer is separated, dried and concentrated to afford 220 mg of B-1.7. ESI-MS: 228 [M+H]⁺; HPLC (Rt): 0.79 min (method M).

Step 5: To a stirred mixture of B-1.7 (100 mg, 0.44 mmol) and DIPEA (0.11 mL, 0.64 mmol) in NMP (2.0 mL) is added at RT B-1.8 (100 mg, 0.55 mmol). The mixture is stirred in microwave at 100° C. for 40 min. The mixture is poured into H₂O and extracted with EA. The organic phase is washer with diluted citric acid, dried and concentrated to afford 180 mg of B-1.9. ESI-MS: 374 [M+H]⁺; HPLC (Rt): 1.45 min (method M).

Step 6: HCl (4 M in dioxane) is added to B-1.9 (180 mg, 0.48 mmol) at RT and the mixture is stirred for 2 h. The solvent is evaporated to afford 100 mg of B-1. ESI-MS: 274 [M+H]⁺; HPLC (Rt): 0.75 min (method M).

N-[(2S)-2-(Ethylamino)propyl]-5-(trifluoromethyl) pyrimidin-2-amine hydrochloride B-2

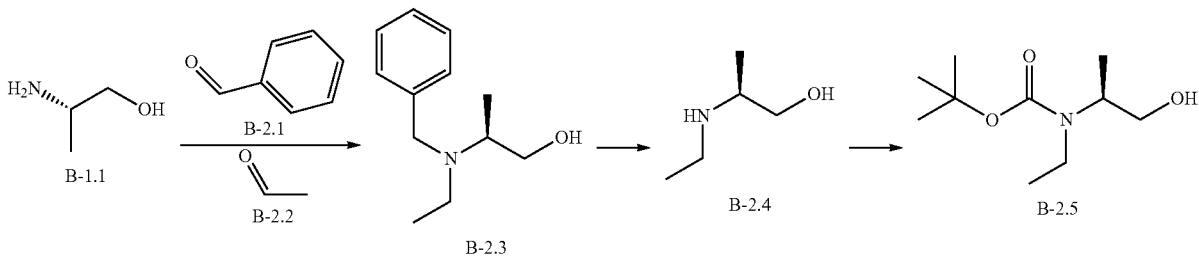

-continued

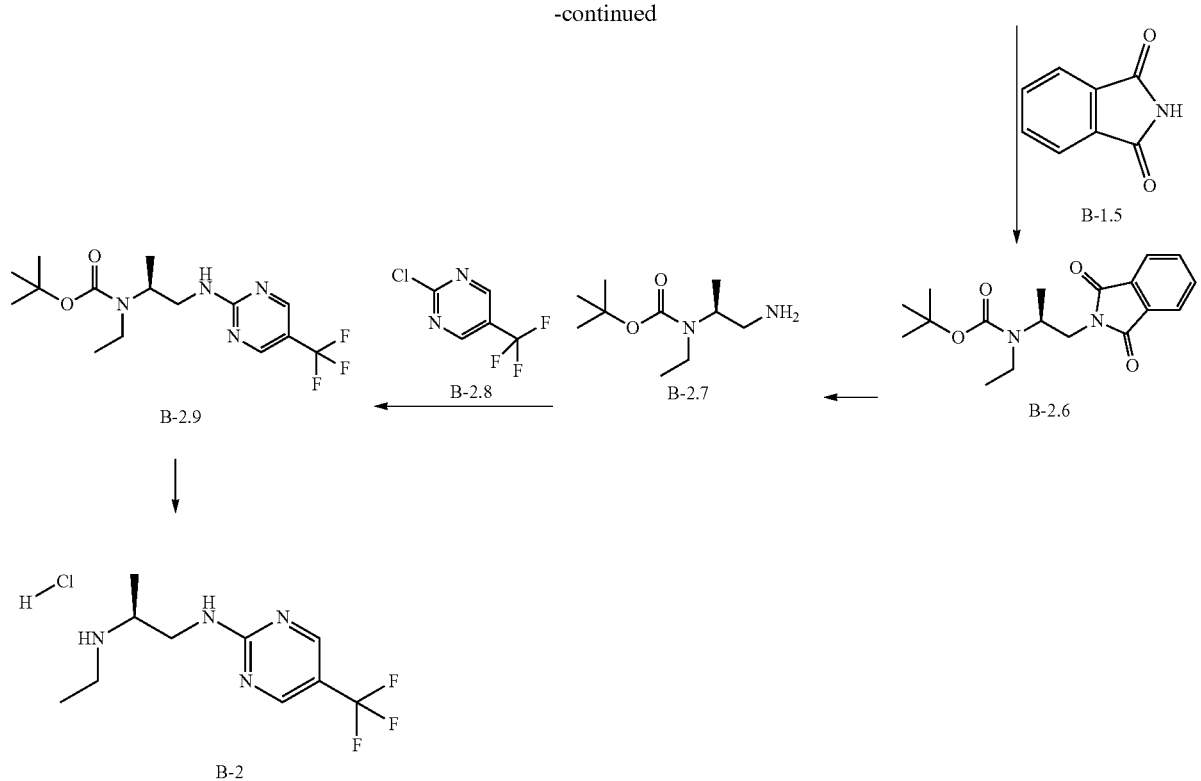

Step 1: A mixture of B-1.1 (5.0 g, 66 mmol), B-2.1 (6.8 mL, 66 mmol) in anhydrous THF (180 mL) is stirred at RT for 1 h. Sodium triacetoxyborohydride (44.6 g, 0.20 mol) is added at 0° C. and the mixture is stirred at RT for 30 min. B-2.2 (11.0 mL, 0.20 mol) in THF (20 mL) is added dropwise within 10 min at 0° C. and the mixture is stirred at RT overnight. Additional B-2.2 (10 mL) is added and stirred at RT for 3 h. The precipitate is filtrated and washed with THF and DCM. NaHCO$_3$ (sat. aq. solution, 200 mL) and solid NaHCO$_3$ are added until gas formation ceases. The aqueous phase is extracted with DCM, dried and concentrated to provide 12.0 g of B-2.3. ESI-MS: 194 [M+H]$^+$; HPLC (Rt): 1.13 min (method C).

Step 2: To a mixture of B-2.3 (3.47 g, 18.0 mmol) in MeOH (4.9 mL) is added Pd/C (350 mg). The mixture is stirred at RT for 16 h under an atmosphere of hydrogen (3 bar). The mixture is filtered through a celite pad and the solvent is evaporated to afford 2.7 g of B-2.4. ESI-MS: 130 [M+H]$^+$; HPLC (Rt): 0.27 min (method I).

Step 3: B-2.4 (3.15 g, 22.6 mmol) and di-tert-butyldicarbonate (5.42 g, 24.8 mmol) are dissolved in THF (100 mL). Under stirring DIPEA (10.0 mL, 58.4 mmol) is added portionwise and the mixture is stirred at RT for 3 h. The mixture is concentrated and the residue is dissolved in DCM. The mixture is washed with H$_2$O, NaOH (1 M aq. solution), HCl (1 M aq. solution) and brine. The organic phase is dried and concentrated. The crude product is purified by flash column chromatography on silica gel (using a solvent gradient from cyclohexane to cyclohexane/EA 6/4) to afford 4.5 g of B-2.5. ESI-MS: 204 [M+H]$^+$; HPLC (Rt): 0.92 min (method I).

Step 4: To a mixture of B-2.5 (4.50 g, 22.1 mmol), B-1.5 (5.00 g, 34.0 mmol) and PPh$_3$ (8.90 g, 33.9 mmol) in dry THF (80 mL) is added DIAD (6.00 mL, 33.2 mmol) dropwise at 0° C. and under a nitrogen atmosphere. The mixture is stirred at RT for 16 h. The solvent is concentrated, the residue is treated with H$_2$O and extracted with EA. The organic layer is separated, dried and concentrated. The residue is purified by flash column chromatography on silica gel (using a solvent mixture of n-hexane/EA/MeOH 70/30/1) to get 4.4 g of B-2.6. ESI-MS: 333 [M+H]$^+$; HPLC (Rt): 1.25 min (method I).

Step 5: MeNH$_2$ (33% in EtOH, 20 mL) is added to B-2.6 (1.20 g, 3.61 mmol) at RT. The mixture is stirred for 20 h. Then cooled on ice bath and the solid is filtered and washed with cold EtOH. The solvent is evaporated and the residue is treated with cold citric acid (10% aq. solution). The mixture is extracted with EA. The organic layer is separated. The water phase is treated with NH$_4$OH and extracted with EA. The organic layer is separated, dried and concentrated to afford 650 mg of B-2.7. ESI-MS: 203 [M+H]$^+$; HPLC (Rt): 0.65 min (method I).

Step 6: To a stirred mixture of B-2.7 (1.88 g, 9.29 mmol) and DIPEA (2.50 mL, 14.6 mmol) in NMP (20 mL) is added at RT under a nitrogen atmosphere B-2.8 (2.20 g, 12.1 mmol). The mixture is stirred in microwave at 100° C. for 30 min. The mixture is poured into H$_2$O and extracted with EA. The organic phase is separated, washed with citric acid (10% aq. solution) and H$_2$O. The organic layer is dried and concentrated. The residue is purified by flash column chromatography on silica gel (using a solvent mixture of n-hexane/EA 80/20) to get 2.7 g of B-2.9. ESI-MS: 349 [M+H]$^+$; HPLC (Rt): 1.34 min (method I).

Step 7: HCl (4 M in dioxane, 40 mL) is added to a stirred mixture of B-2.9 (5.50 g, 15.8 mmol) in dioxane (10 mL) at RT and the mixture is stirred for 2 h. The solvent is evaporated. The residue is treated with EA and the solid is filtered to afford 3.5 g of B-2. ESI-MS: 249 [M+H]$^+$; HPLC (Rt): 0.63 min (method I).

N-[(2S)-2-(Ethylamino)propyl]-5-(trifluoromethyl)pyrazin-2-amine hydrochloride B-3

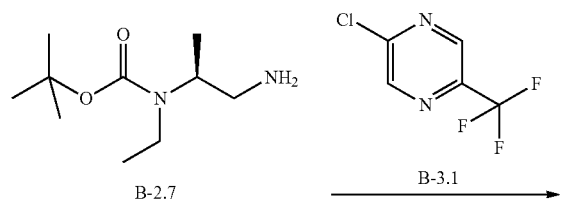

B-2.7     B-3.1

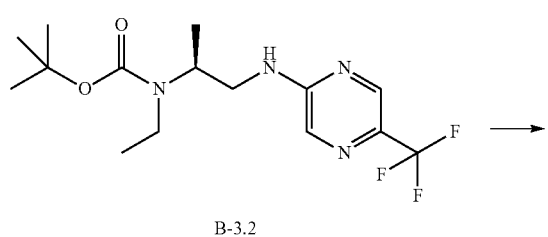

B-3.2

Step 1: To a stirred mixture of B-2.7 (1.00 g, 4.90 mmol) and DIPEA (1.4 mL, 8.0 mmol) in NMP (8.0 mL) is added at RT under a nitrogen atmosphere B-3.1 (0.8 mL, 6.4 mmol). The reaction is heated at 100° C. in microwave for 30 min. The reaction is poured into water and extracted with EA. The organic layer is separated, washed with citric acid (10% aq. solution) and water. The organic layer is dried and concentrated. The residue is purified by flash column chromatography on silica gel (using CH/EA 80/20 as eluent). After evaporation 1.0 g of B-3.2 is obtained. ES+/−: 349 [M+H]$^+$; HPLC (Rt): 1.36 min (method I).

Step 2: HCl (4M in dioxane, 20 mL) is added to a mixture of B-3.2 (1.50 g, 4.30 mmol) in dioxane (5.0 mL) at 0° C. then it is stirred at RT overnight. The solvent is removed and the residue is treated with Et$_2$O to afford 830 mg of B-3. ES+/−: 249 [M+H]$^+$; HPLC (Rt): 0.67 min (method I).

The following examples are prepared in analogy to the above described procedure using the starting materials as described in the table. For Amine B-4 the reaction mixture is stirred at RT for 4 h.

| Amine | Starting Material | Structure Amine | ESI-MS [M + H]$^+$ | HPLC (Rt) [min] | HPLC Method |
|---|---|---|---|---|---|
| B-4 | ![B-4 SM] | ![B-4 structure] | 260 | 2.33 | L |

(S)—N*2*-Methyl-N*1*-(trifluoromethyl-pyrimidin-2-yl)-propane-1,2-diamine hydrochloride B-5

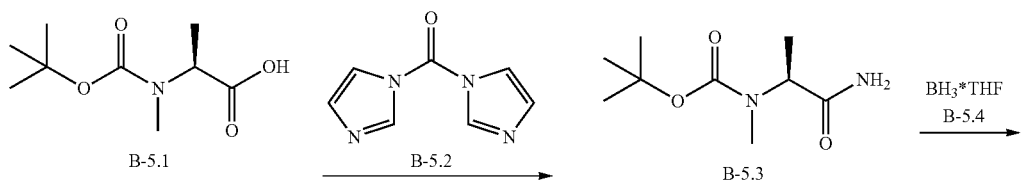

B-5.1     B-5.2     B-5.3     B-5.4

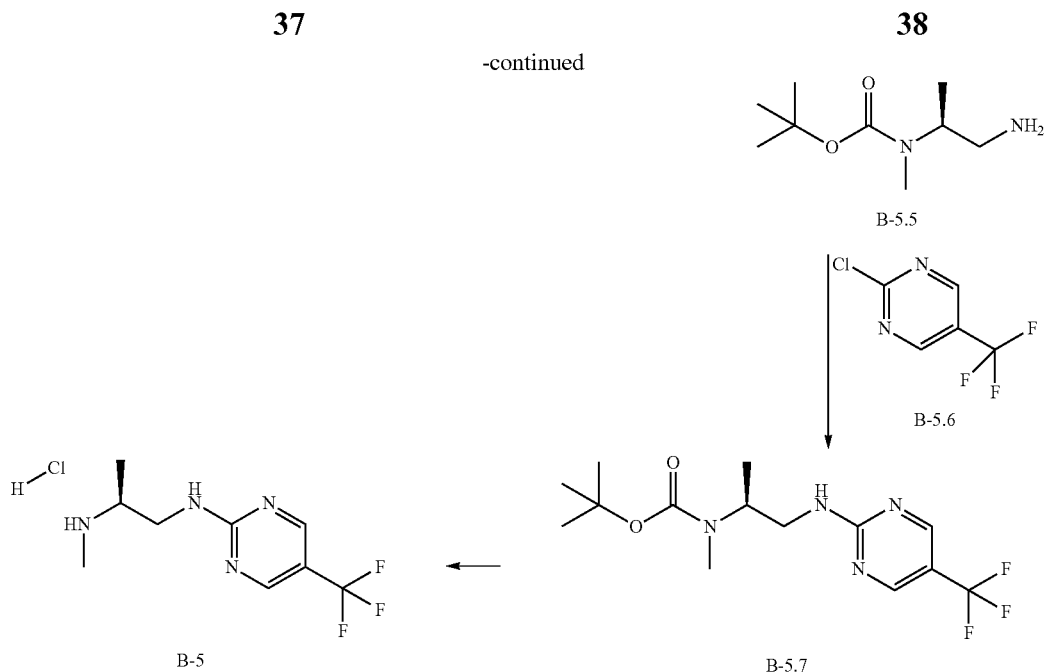

Step 1: B-5.1 (740 mg, 3.64 mmol) is added to a mixture of B-5.2 (830 mg, 5.12 mmol) in dry THF at 0° C. under nitrogen atmosphere. The reaction is warmed to RT and stirred for 2 h. Then NH₄OH is added and after 1 h the solvent is removed. The residue is treated with NaHCO₃ (aq. solution) and extracted with DCM. The organic phase is dried and concentrated to afford 640 mg of B-5.3. ESI-MS: 202 [M+H]⁺; HPLC (Rt): 0.72 min (method M).

Step 2: B-5.3 (9.20 mL, 9.20 mmol) is added to B-5.4 (620 mg, 3.07 mmol) in dry THF at 0° C. under nitrogen atmosphere. The reaction mixture is heated at reflux for 3 h. After cooling at 0° C. MeOH is added and the solvent is reduced. The residue is treated with water and extracted with DCM. The organic phase is dried and concentrated to afford 580 mg B-5.5. ESI-MS: 188 [M+H]⁺; HPLC (Rt): 0.64 min (method M).

Step 3: To a stirred mixture of B-5.5 (580 mg, 3.08 mmol) and B-5.6 (680 mg, 3.73 mg) in NMP (15 mL) is added DIPEA (0.68 mL, 3.97 mmol) at RT under a nitrogen atmosphere. The mixture is stirred at 100° C. for 1 h. After cooling the mixture is poured into H₂O and extracted with EA. The organic phase is dried and concentrated. The crude product is purified by flash column chromatography on silica gel (using a solvent n-hexane/EA 7/3) to get 340.0 mg of B-5.7. ESI-MS: 334 [M+H]⁺; HPLC (Rt): 1.91 min (method N).

Step 4: HCl (4 M in dioxane, 12 mL) is added to a mixture of B-5.7 (330.0 mg, 0.99 mmol) in dioxane (3.0 mL) and the mixture is stirred at RT for 3 h. The solvent is removed and the residue is treated with Et₂O. The organic phase is treated with NH₄OH and extracted with DCM. The organic phase is dried and concentrated to afford 210.0 mg of B-5. ES+/−: 234[M+H]⁺; HPLC (Rt): 0.63 min (method M).

N-[(S)-2-Amino-1-methyl-ethyl]-3-fluoro-N-(2-fluoro-ethyl)-2-[1,2,3]triazol-2-yl-benzamide B-6

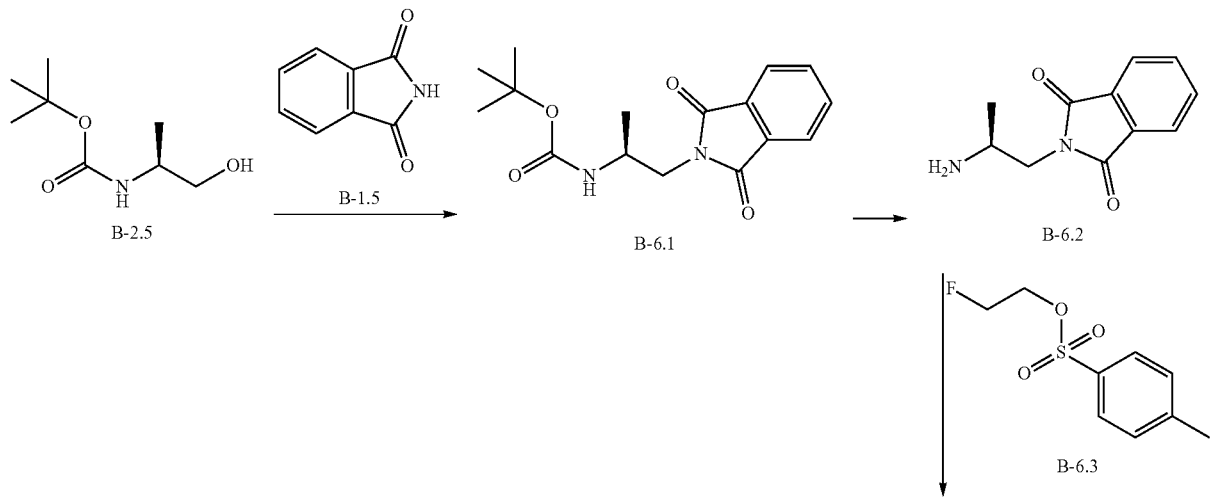

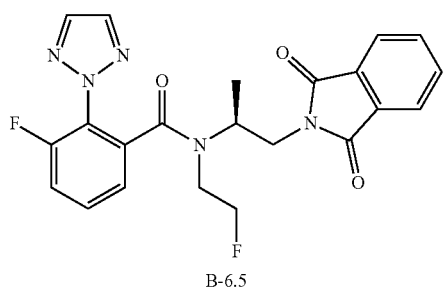
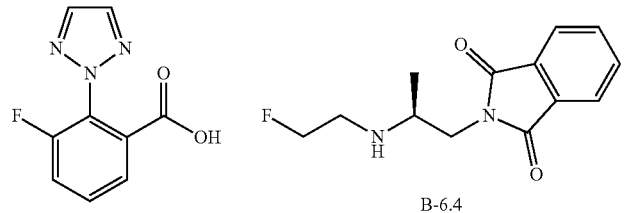

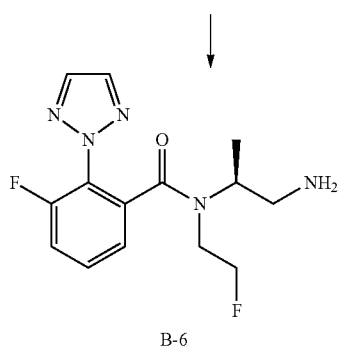

Step 1: To a mixture of B-2.5 (2.00 g, 11.4 mmol), B-1.5 (2.20 g, 14.9 mmol) and PPh$_3$ (3.90 g, 14.9 mmol) in dry THF (180 mL) is added dropwise at 0° C. under N$_2$ atmosphere DIAD (3.0 mL, 16.6 mmol). The reaction mixture is warmed to RT and stirred for 16 h. The reaction mixture is concentrated and the residue is treated with water and extracted with EA. The organic layer is separated, dried and concentrated. The residue is purified by flash column chromatography on silica gel (using a solvent mixture of n-hexane/EA 70/30) to get 3.4 g of B-6.1. ESI-MS: 304 [M+H]$^+$; HPLC (Rt): 1.05 min (method M).

Step 2: To B-6.1 (2.00 g, 6.57 mmol) in dry dioxane is added HCl in dioxane (4 M, 40.0 mL, 40.0 mmol) and stirred at RT for 3 h. The residue is treated with water and extracted with diethylether. The aqueous layer is treated with NH$_4$OH (aq. solution) and extracted with DCM. The organic layer is separated and concentrated to afford 600 mg of B-6.2. ESI-MS: 204 [M+H]$^+$; HPLC (Rt): 0.54 min (method M).

Step 3: To a mixture of B-6.2 (560 mg, 2.74 mmol), DIPEA (0.70 ml, 4.09 mmol) and KI (560 mg, 3.31 mmol) in DMF (63.0 mL) is added B-6.3 (720 mg, 3.30 mmol). The reaction mixture is stirred under N$_2$ atmosphere at 100° C. for 6 h. The reaction mixture is treated with water and extracted with EA. The organic layer is separated, dried and concentrated. The residue is purified by flash column chromatography on silica gel (using a solvent mixture of DCM/ MeOH/NH$_4$OH 98/2/0.2) to get 120 mg of B-6.4. ESI-MS: 250 [M+H]$^+$; HPLC (Rt): 0.73 min (method M).

Step 4: To a mixture of B-6.4 (120 mg, 0.48 mmol) and A-1 (120 mg, 0.58 mmol) in dry ACN is added DIPEA (240 µL, 1.40 mmol) and after 20 min CIP (200 mg, 0.72 mmol) is added and the mixture is stirred at RT for 18 h. The reaction mixture is treated with water and extracted with EA. The organic layer is separated, dried and concentrated. The residue is purified by flash column chromatography on silica gel (using a solvent mixture of n-hexane/EA/MeOH 70/30/ 1) to get 80.0 mg of B-6.5. ESI-MS: 439 [M+H]$^+$; HPLC (Rt): 1.02 min (method M).

Step 5: To a mixture of B-6.5 (80.0 mg, 0.18 mmol) in dry EtOH (24.0 mL) is added at RT N$_2$H$_4$×H$_2$O (40.0 µL, 52.0 mmol) and the reaction is stirred for 20 h. The reaction mixture is cooled in ice water and the solid is filtered and washed with cold EtOH. The solvent is evaporated and the residue is treated with cold citric acid and extracted with EA. The organic layer is separated and the aqueous layer is treated with NH$_4$OH (aq. solution) and extracted with EA. The combined organic layers are dried end concentrated to afford 45.0 mg of B-6. ESI-MS: 309 [M+H]$^+$; HPLC (Rt): 0.62 min (method M).

N-((S)-2-Amino-1-methyl-ethyl)-N-ethyl-5-fluoro-2-[1,2,3]triazol-2-yl-nicotinamide B-7

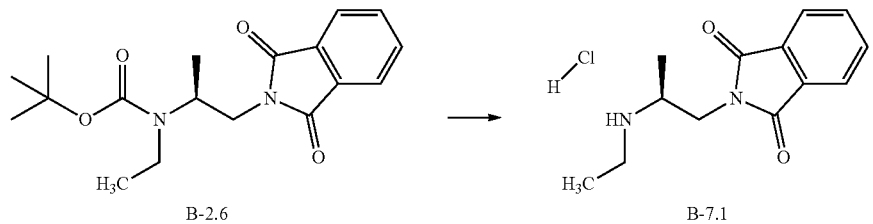

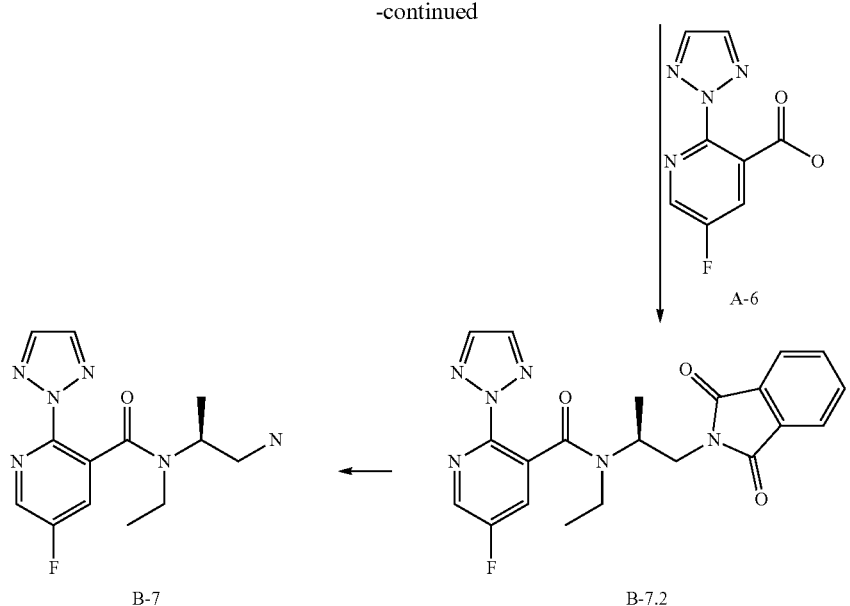

Step 1: HCl (4 M in dioxane, 7.37 mL, 29.5 mmol) is added to a stirred mixture of B-2.6 (980 mg, 2.95 mmol) in dioxane (10 mL) at RT and the mixture is stirred for overnight. The solvent is evaporated and treated with Et₂O to afford 750 mg of B-7.1. HPLC (Rt): 0.60 min (method M).

Step 2: To B-7.1 (750 mg, 2.79 mmol) in ACN (3.0 mL) A-6 (640.0 mg, 3.07 mmol), DIPEA (1.44 mL, 8.37 mmol) and CIP (1.01 g, 3.63 mmol) are added and stirred at RT overnight. The reaction mixture is evaporated and the residue is diluted in DCM and washed with water. The organic phase is concentrated and the crude product is purified by flash column chromatography on silica gel (using a solvent gradient from n-hexane/EA 4/6) to afford 1.1 g of B-7.2. HPLC (Rt): 0.90 min (method M).

Step 3: Hydrazine hydrate (3.0 mL, 39.0 mmol) is added to B-7.2 (1.05 g, 2.49 mmol) in dry EtOH (15.0 mL) at RT. The mixture is stirred overnight. The solid is filtered and washed with cold EtOH. The solvent is removed and the residue is treated with cold citric acid. The solution is extracted with EA. The aqueous phase is treated with NH₄OH to pH 10 and extracted with EA and DCM/MeOH 9/1. The organic phase is dried and concentrated to get 260 mg of B-7. HPLC (Rt): 0.58 min (method M).

N-[(2S)-1-aminopropan-2-yl]-N-ethyl-3-fluoro-2-(2H-1,2,3-triazol-2-yl)benzamide B-8

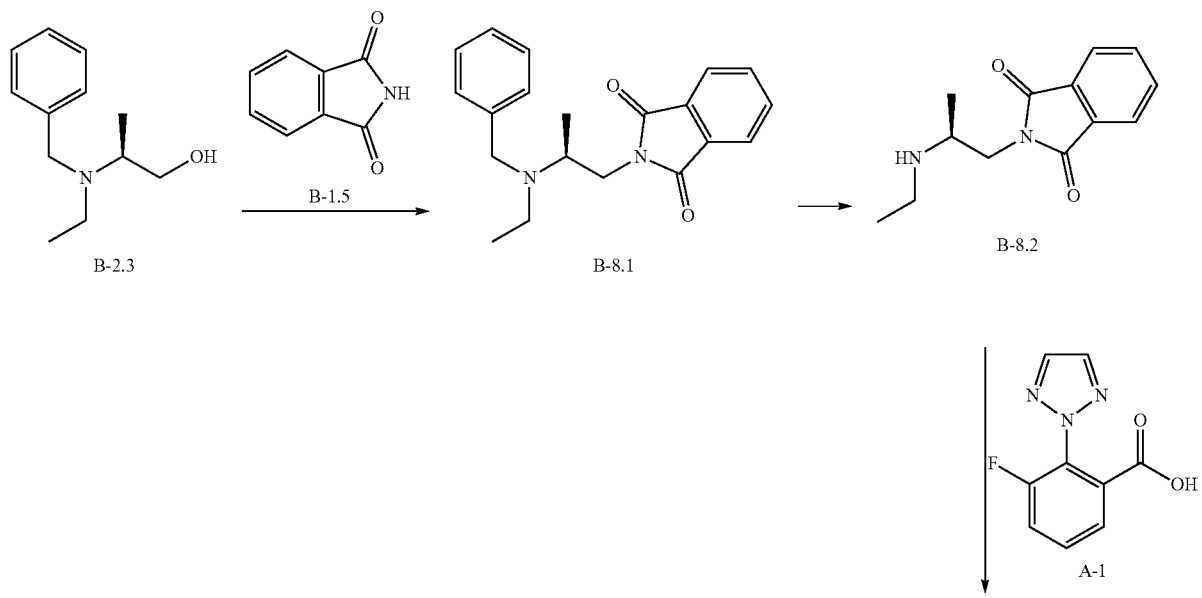

-continued

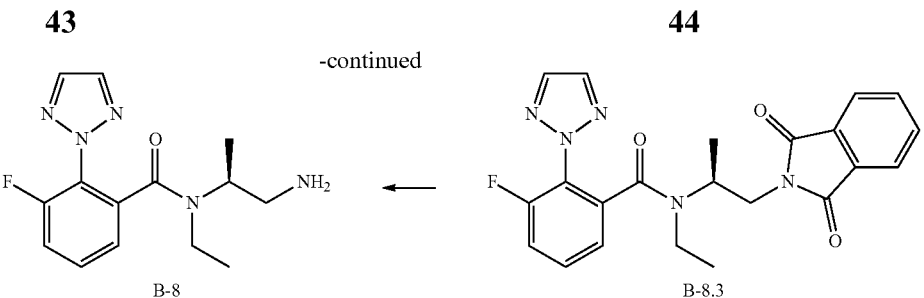

Step 1: To a mixture of B-2.3 (10.0 g, 0.05 mol) and B-1.5 (7.60 g, 0.05 mol) in THF (150 mL) is added PPh$_3$ (13.6 g, 0.05 mol). Then DIAD (8.80 g, 0.05 mol) is added dropwise at 0° C. The mixture is stirred at RT for 12 h. The reaction mixture is concentrated and the residue is purified by flash column chromatography on silica gel (using petroleum ether/EA from 20/1 to 10/1) to afford 10 g of B-8.1.

Step 2: To a mixture of B-8.1 (2.00 g, 10 mmol) in MeOH (30 mL) is added Pd/C (1.0 g). The mixture is stirred at 20° C. for 12 h under an atmosphere of hydrogen (50 psi). The mixture is filtered and the filtrate is concentrated to afford 800 mg of B-8.2.

Step 3: To a mixture of B-8.2 (2.50 g, 9.30 mmol) in dry ACN (50 mL) is added A-1 (2.30 g, 11.0 mmol), DIPEA (4.8 mL, 28 mmol) and CIP (3.1 g, 11 mmol) and the mixture is stirred at RT for 2 h. Another portion of A-1 (200 mg) and CIP (500 mg) are added and the reaction is stirred for another 2 h. Then another portion of DIPEA (1.5 mL) and CIP (300 mg) are added and the reaction is stirred for 2 h. Water (70 mL) is added to the reaction mixture is stirred for 1 h. The precipitate is filtered and dried. The mother liquid is extracted with EA, dried and concentrated. The residue is purified by prep. HPLC (using a solvent gradient H$_2$O/ACN with NH$_4$OH) and combined with the dried solid to provide 3.4 g of B-8.3. ESI pos.+neg. (Loop-Inj.) [M+H]$^+$: 422; HPLC (Rt): 0.97 min (method D).

Step 5: To a mixture of B-8.3 (3.4 g, 8.0 mmol) in EtOH (100 mL) is added at RT N$_2$H$_4$×H$_2$O (1.2 mL, 20 mmol) and the reaction is stirred overnight. Another portion of N$_2$H$_4$× H$_2$O (0.50 mL) is added and the reaction is stirred at 60° C. for 2 h. The solid is filtered. The solvent is evaporated and the residue is dissolved in EA and extracted with HCl (1 M aq. solution). The acidic aqueous layer is washed with EA, then the pH is adjusted with NH$_4$OH (25% aq. solution) to pH=10. The aqueous phase is extracted with EA, dried and concentrated to afford 2.1 g of B-8. ESI pos.+neg. (Loop-Inj.) [M+H]$^+$: 292 [M+H]$^+$; HPLC (Rt): 0.70 min (method K).

Preparation of Compounds of the Present Invention

Example 1

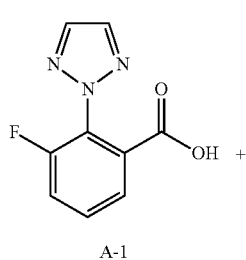

A-1

-continued

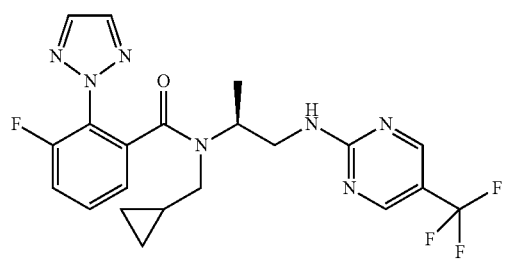

B-1

Example 1

CIP (130 mg, 0.47 mmol) is added to a stirred mixture of A-1 (100 mg, 0.36 mmol), B-1 (85 mg, 0.41 mmol) and DIPEA (180 µL, 1.0 mmol) in dry ACN (4.5 mL) at RT. After 18 h the reaction is treated with water and extracted with EA. The organic phase was separated, washed with water, dried over Na$_2$SO$_4$ and concentrated. The residue is purified by preparative LCMS to afford 90 mg of compound Example 1. ESI-MS: 464 [M+Na]$^+$; HPLC (Rt): 3.67 min (method E).

Example 2

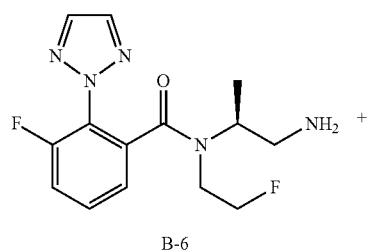

B-6

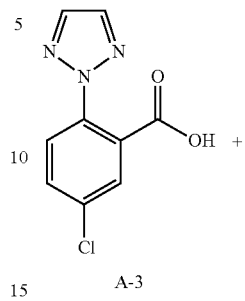

B-5.6

Example 2

To a stirred mixture of B-6 (35 mg, 0.091 mmol) in NMP (2 mL), B-5.6 (25 mg, 0.14 mmol) and DIPEA (0.025 mL, 0.15 mmol) are added at RT under a nitrogen atmosphere. The reaction is heated at 100° C. in a microwave for 40 min. After cooling the reaction is poured into water an extracted with EA. The organic layer is separated, washed with citric acid (10% aq. solution), dried and concentrated. The residue is purified by LCMS to afford 15 mg of Example 2. ESI-MS: 456 [M+H]$^+$; HPLC (Rt): 3.40 min (method E).

Example 3

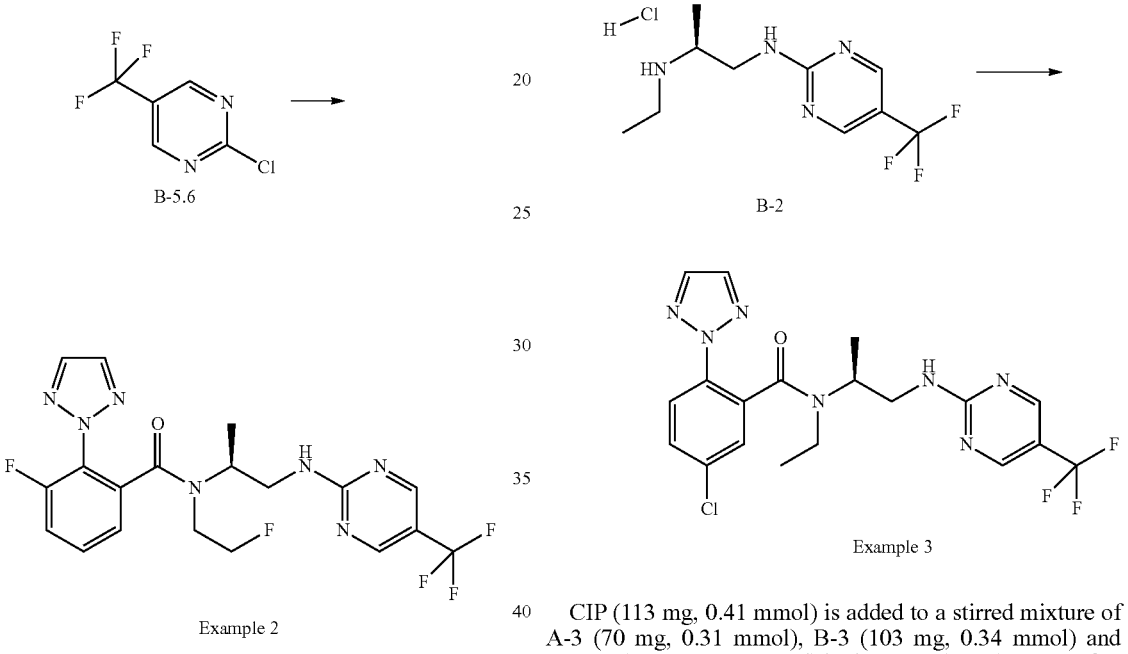

A-3

B-2

Example 3

CIP (113 mg, 0.41 mmol) is added to a stirred mixture of A-3 (70 mg, 0.31 mmol), B-3 (103 mg, 0.34 mmol) and DIPEA (162 µL, 0.94 mmol) in dry ACN (3 mL) at RT. After 2 h the reaction is treated with water and extracted with EA. The organic phase was separated, washed with water, dried over Na$_2$SO$_4$ and concentrated. The residue is purified by preparative LCMS (using a solvent gradient H$_2$O/ACN with NH$_4$OH) to afford 128 mg of compound Example 3. ESI-MS: 454 [M+H]$^+$; HPLC (Rt): 1.53 min (method I).

The following example is prepared in analogy to the above described procedure using the corresponding acid (see Acid Intermediates) and amine (see Amine Intermediates) as described before.

| Example | Structure | ESI-MS [M + H]$^+$ | HPLC (Rt) [min] | HPLC Method |
|---|---|---|---|---|
| 11 | 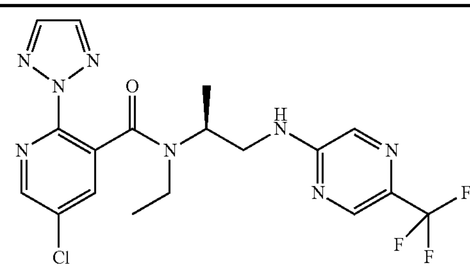 | 455 | 4.05 | L |

Example 4

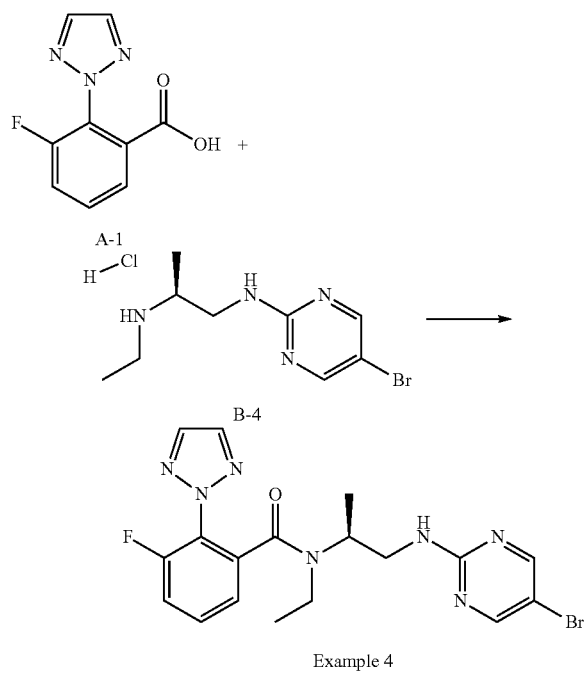

Example 4

CIP (49 mg, 0.18 mmol) is added to a stirred mixture of A-1 (34 mg, 0.16 mmol), B-4 (40 mg, 0.14 mmol) and DIPEA (70 μL, 0.41 mmol) in dry ACN (2.0 mL) at RT. After 2 h the reaction is treated with ACN/water and purified by preparative LCMS (using a solvent gradient $H_2O$/ACN with $NH_4OH$) to afford 20 mg of compound Example 4. ESI-MS: 448 [M+H]$^+$; HPLC (Rt): 0.99 min (method G).

The following examples are prepared in analogy to the above described procedure using the corresponding acid (see Acid Intermediates) and amine (see Amine Intermediates) as described before.

Example 7

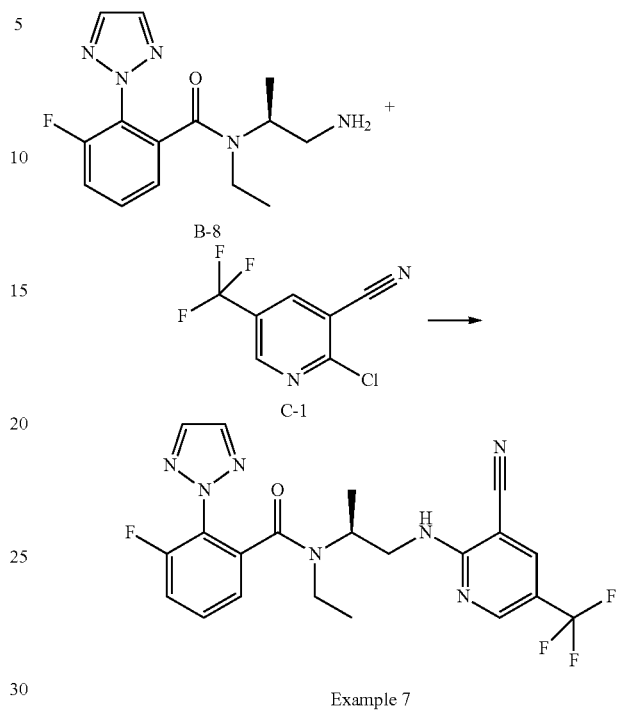

Example 7

To a stirred mixture of B-8 (30 mg, 0.10 mmol) in NMP (2 mL), C-1 (21 mg, 0.10 mmol) and DIPEA (0.027 mL, 0.15 mmol) are added at RT under a nitrogen atmosphere. The reaction is heated at 120° C. for 3 h. After cooling the reaction is poured into water an extracted with EA. The organic layer is separated, washed with citric acid (10% aq. solution), dried and concentrated. The residue is purified by preparative LCMS (using a solvent gradient $H_2O$/ACN with $NH_4OH$) to afford 28 mg of Example 7. ESI-MS: 462 [M+H]$^+$; HPLC (Rt): 0.88 min (method J).

| Example | Structure | ESI-MS [M + H]$^+$ | HPLC (Rt) [min] | HPLC Method |
|---------|-----------|--------------------|------------------|-------------|
| 5 | 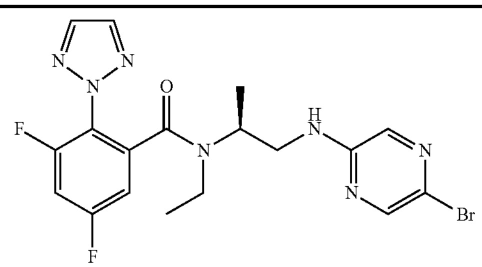 | 466 | 1.01 | D |
| 13 | 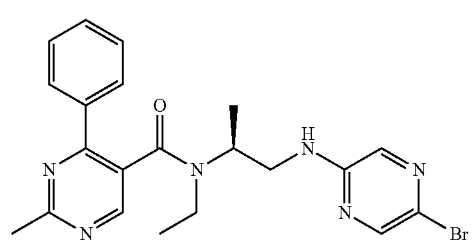 [SMILES: CCN(C(=O)c1cnc(C)nc1-c1ccccc1)[C@@H](C)CNc1cnc(Br)cn1] | 455 | 1.01 | D |

The following examples are prepared in analogy to the above described procedure using the corresponding amine (see Amine Intermediates) and appropriate aryl halides as described before. For Example 12 the procedure and purification is adapted: the reaction is heated in a microwave at 100° C. for 30 min. The residue is purified by LCMS (using a solvent gradient H₂O/ACN with NH₄OH).

A mixture of A-8 (373 mg, 1.58 mmol), B-2 (300 mg, 1.05 mmol) and DIPEA (0.73 mL; 4.22 mmol) in DMF (2.0 mL) is stirred very well and heated to 70° C. At this temperature T3P (0.24 mL, 2.11 mmol) is added and the reaction mixture is stirred at 70° C. overnight. The reaction mixture is diluted with DMF/MeOH and purified by preparative LCMS (using

| Example | Structure | ESI-MS [M + H]⁺ | HPLC (Rt) [min] | HPLC Method |
|---|---|---|---|---|
| 6 | 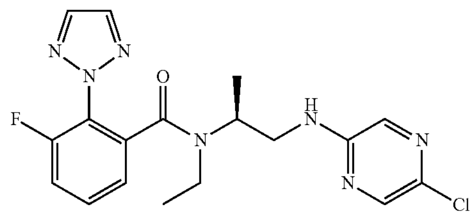 [SMILES: CCN(C(=O)c1cccc(F)c1-n1nccn1)[C@@H](C)CNc1cnc(Cl)cn1] | 404 | 0.76 | J |
| 12 | 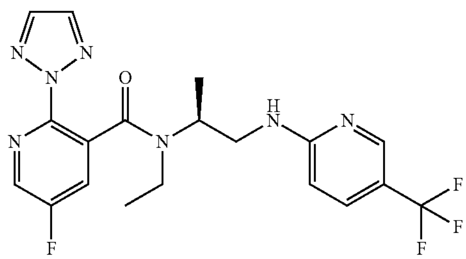 [SMILES: CCN(C(=O)c1cc(F)cnc1-n1nccn1)[C@@H](C)CNc1ccc(C(F)(F)F)cn1] | 438 | 3.19 | E |

Example 8

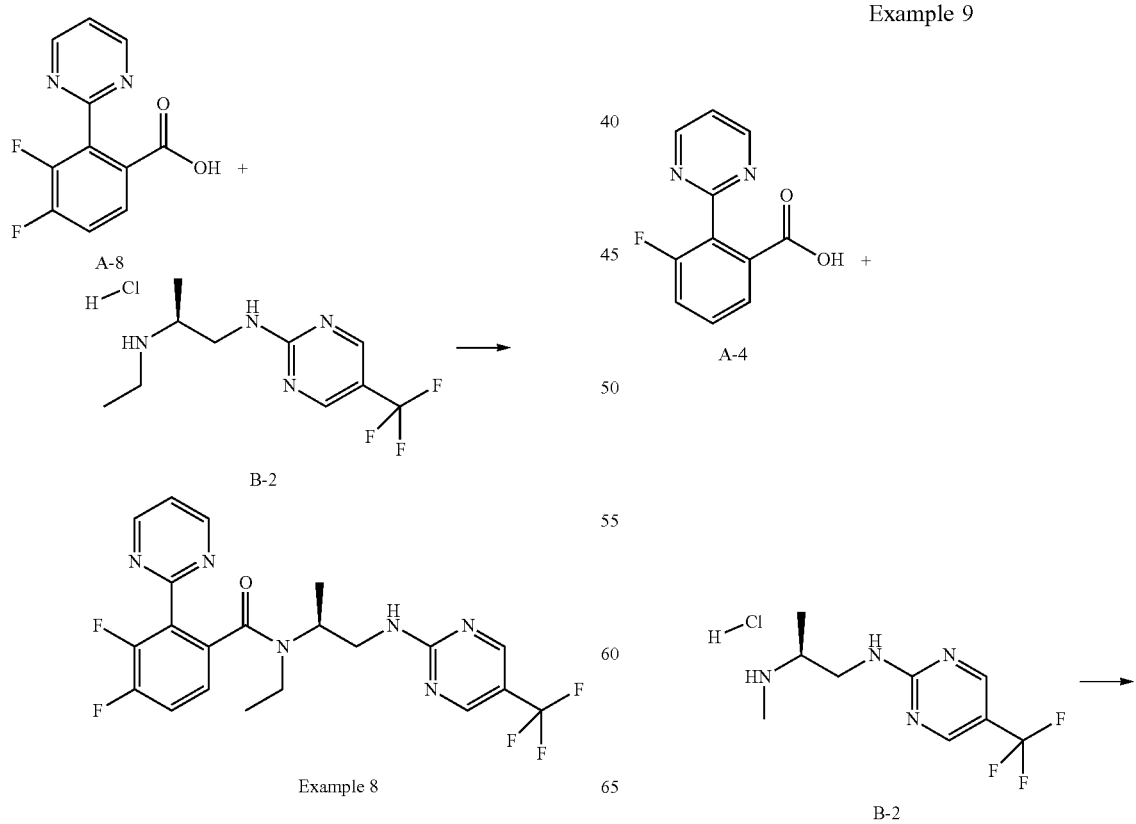

a solvent gradient H₂O/ACN with NH₄OH) to afford 110 mg of Example 8. ESI-MS: 467 [M+H]⁺; HPLC (Rt): 1.01 min (method D).

Example 9

Example 9

2-Chloro-4,6-dimethoxy-1,3,5-triazine (70 mg, 0.30 mmol) is added to a stirred mixture of A-4 (80 mg, 0.30 mmol), B-2 (80 mg, 0.37 mmol) and N-methylmorpholine (50 µL, 0.45 mmol) in dry ACN (2.4 mL) at RT and the reaction mixture was heated to 50° C. After 3 h the reaction is treated with water, extracted with EA and the organic phase dried over $Na_2SO_4$ and concentrated. The residue is purified by preparative LCMS to afford 40 mg of Example 9. ESI-MS: 435 $[M+H]^+$; HPLC (Rt): 3.04 min (method I).

Example 10

Example 10

CIP (65 mg, 0.23 mmol) is added to a stirred mixture of A-3 (40 mg, 0.18 mmol), B-3 (59 mg, 0.20 mmol) and DIPEA (92 µL, 0.54 mmol) in dry ACN (3 mL) at RT. After 2 h the reaction is treated with water and extracted with EA. The organic phase was separated, washed with water, dried over $Na_2SO_4$ and concentrated. The residue is purified by preparative LCMS (using a solvent gradient $H_2O$/ACN with $NH_4OH$) to afford 52 mg of compound Example 10. ESI-MS: 454 $[M+H]^+$; HPLC (Rt): 4.65 min (method L).

The invention claimed is:

1. A compound selected from the group consisting of:

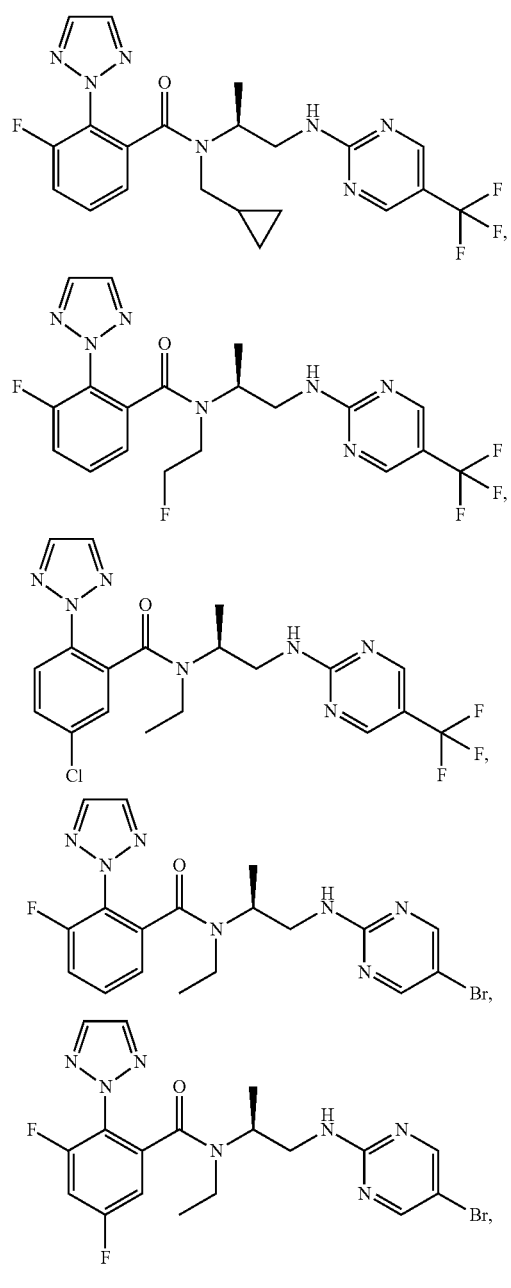

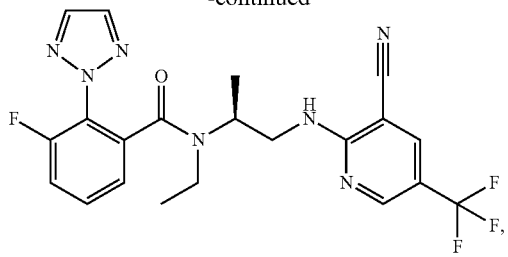
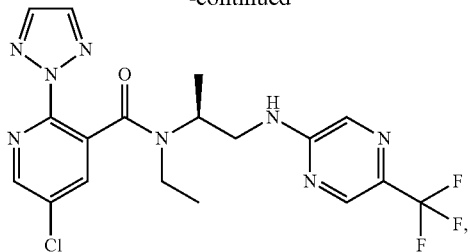
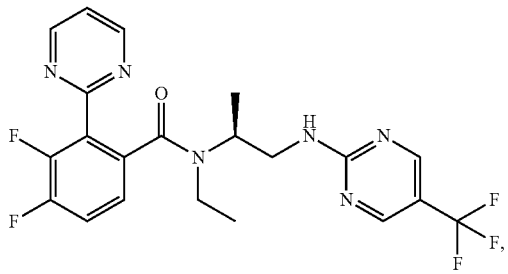
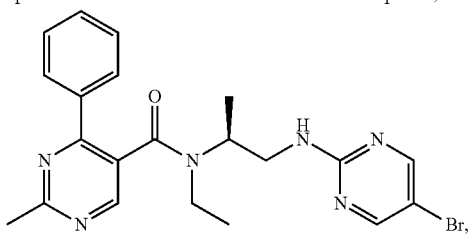
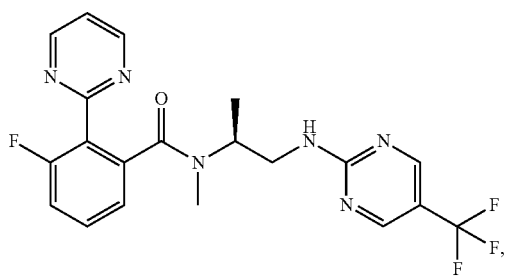

, and

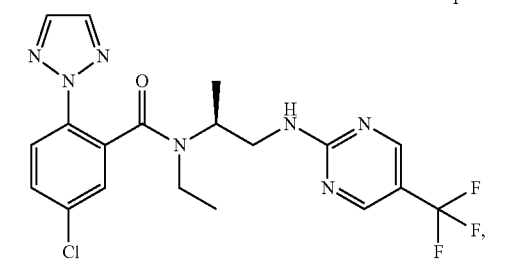

or a pharmaceutically acceptable salt thereof.

2. The compound according to claim 1 in form of a pharmaceutically acceptable salt.

3. The compound according to claim 1 in the form of a free acid or free base.

4. A pharmaceutical composition comprising the compound according to claim 3 in admixture with a pharmaceutically acceptable adjuvant, diluent and/or carrier.

5. A pharmaceutical composition comprising the compound according to claim 2 in admixture with a pharmaceutically acceptable adjuvant, diluent and/or carrier.

* * * * *